(12) United States Patent
Dahlberg et al.

(10) Patent No.: US 7,700,288 B2
(45) Date of Patent: Apr. 20, 2010

(54) MIR-155 ASSAY

(75) Inventors: James E. Dahlberg, Madison, WI (US);
Peggy S. Eis, Fitchburg, WI (US);
Wayne Tam, Forest Hills, NY (US);
Elsebet Lund, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/352,837

(22) Filed: Feb. 13, 2006

(65) Prior Publication Data

US 2006/0199233 A1 Sep. 7, 2006

Related U.S. Application Data

(60) Provisional application No. 60/652,301, filed on Feb. 11, 2005, provisional application No. 60/656,245, filed on Feb. 25, 2005.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

2004/0018566 A1 1/2004 Vallone et al.

OTHER PUBLICATIONS

Metzler et al., "High Expression of Precursor MicroRNA-155/BIC RNA in Children with Burkitt Lymphoma," Genes, Chromosomes & Cancer 39:2167-169(2004).

Van Den Berg., "High Expression of B-Cell Receptor Inducible Gene BIC in all Subtypes of Hodgkin Lymphoma," Genes, Chromosomes & Cancer 37:20-28 (2003).

McManus et al., "MicroRNAs and cancer," Seminars in Cancer Biology, Saunders Scientific Publications, 13:4253-258 (2003).

Eis et al., "Accumulation of miR-155 and BIC RNA in human B cell lymphomas," PNAS 102:3627-632 (Mar. 8, 2005).

Allawi et al., "Quanitation of microRNAs using a modified Invader assay," RNA, Cold Spring Harbor Laboratory Press, 10:71153-1161 (2004).

Rosenwald et al., "Molecular Diagnosis of Primary Mediastinal B Cell Lymphoma Identifies a Clinically Favorable Subgroup of Diffuse Large B Cell Lymphoma Related to Hodgkin Lymphoma," Journal of Experimental Medicine 198:851-862 (2003).

*Primary Examiner*—Misook Yu
(74) *Attorney, Agent, or Firm*—McDonnell Boehnen Hulbert & Berghoff

(57) ABSTRACT

The invention provides methods for diagnosing B-cell lymphoma in an animal. In particular, the invention provides methods for distinguishing an animal having diffuse large B-cell lymphoma (DLBCL) with an activated B-cell (ABC) phenotype from an animal having DLBCL with a non-activated germinal-center (GC) phenotype. The invention also provides methods for identifying compounds for treating B-cell lymphoma. The invention further provides reagents and methods for determining the amount of miR-155 in sample isolated from an animal. In this regard, the invention provides a set of oligonucleotides for determining the amount of miR-155 in sample isolated from an animal.

12 Claims, 10 Drawing Sheets

FIG. 2A

```
   1                                                                CGCGGGC
   8 TTCCTGTGCG CGGCCGAGCC CGGGCCCAGC GCCGCCTGCA GCCTCGGGAA GGGAGCGGAT
  68 AGCGGAGCCC CGAGCCGCCC GCAGAGCAAG CGCGGGGAAC CAAGGAGACG CTCCTGGCAC

Intron 1
        \7577 nt/                                        A
 128 TGCAGATAAC TTGTCTGCAT TCAAGAACA ACCTACCAGA GACCTTACCT GTCACCTTGG Intron 2           B
                \3912 nt..ctgtcactccagctttataaccgc..35 nt/
 188 CTCTCCCACC GAATGGAGAT CGGCTGTAATG CTGGGACAAA CCAGGAAGGG GAAATCTGTG 248 GTTTAAATTC TTTATGCCTC ATCCTCTGAG TGCTGAAGGC TTGCTGTAGG CTGTATGCTG
                -------------miR-155-------------
 308 TTAATGCTAA TCGTGATAGG GGTTTTTGCC TCCAACTGAC TCCTACATAT TAGCATTAAC

368 AGTGTATGAT GCCTGTTACT AGCATTCACA TGGAACAAAT TGCTGCCGTG GGAGGATGAC

428 AAAGAAGCAT GAGTCACCCT GCTGGATAAA CTTAGACTTC AGGCTTTATC ATTTTTCAAT

488 CTGTTAATCA TAATCTGGTC ACTGGGATGT TCAACCTTAA ACTAAGTTTT GAAAGTAAGG
                                                                       C
 548 TTATTTAAAA GATTTATCAG TAGTATCCTA AATGCAAACA TTTTCATTTA AATGTCAAGC

608 CCATGTTTGT TTTTATCATT AACAGAAAAT ATATTCATGT CATTCTTAAT TGCAGGTTTT

668 GGCTTGTTCA TTATAATGTT CATAAACACC TTTGATTCAA CTGTTAGAAA TGTGGGCTAA
 728 ACACAAATTT CTATAATATT TTTGTAGTTA AAAATTAGAA GGACTACTAA CCTCCAGTTA
 788 TATCATGGAT TGTCTGGCAA CGTTTTTTAA AAGATTTAGA AACTGGTACT TTCCCCCAGG
 848 TAACGATTTT CTGTTCAGGC AACTTCAGTT TAAAATTAAT ACTTTTATTT GACTCTTAAA
 908 GGGAAACTGA AAGGCTATGA AGCTGAATTT TTTAATGAA ATATTTTAA CAGTTAGCAG
 968 GGTAAATAAC ATCTGACAGC TAATGAGATA TTTTTTCCAT ACAAGATAAA AAGATTTAAT
1028 GAAAAATTTG ATATTTGAAA TCAAGTCGGA AATCTAGGTT CAAGTTCAAT AGCTTAGCCA
1088 CATAATACGG TTGTGCGAGC AGAGAATCTA CCTTTCCACT TCTAAGCCTG TTTCTTCCTC
1148 CATAAAATGG GGATAATACT TTACAAGGTT GTTGTGAGGC TTAGATGAGA TAGAGAATTA
1208 TTCCATAAGA TAATCAAGTG CTACATTAAT GTTATAGTTA GATTAATCCA AGAACTAGTC
1268 ACCCTACTTT ATTAGAGAAG AGAAAAGCTA ATGATTTGAT TTGCAGAATA TTTAAGGTTT
1328 GGATTTCTAT GCAGTTTTTC TAAATAACCA TCACTTACAA ATATGTAACC AAACGTAATT
1388 GTTAGTATAT TTAATGTAAA CTTGTTTTAA CAACTCTTCT CAACATTTTG TCCAGGTTAT
1448 TCACTGTAAC CAAATAAATC TCATGAGTCT TTAGTTGATT T
```

FIG. 2B

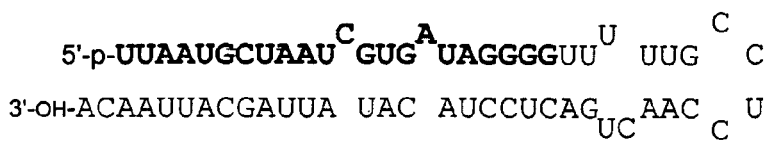

FIG. 3
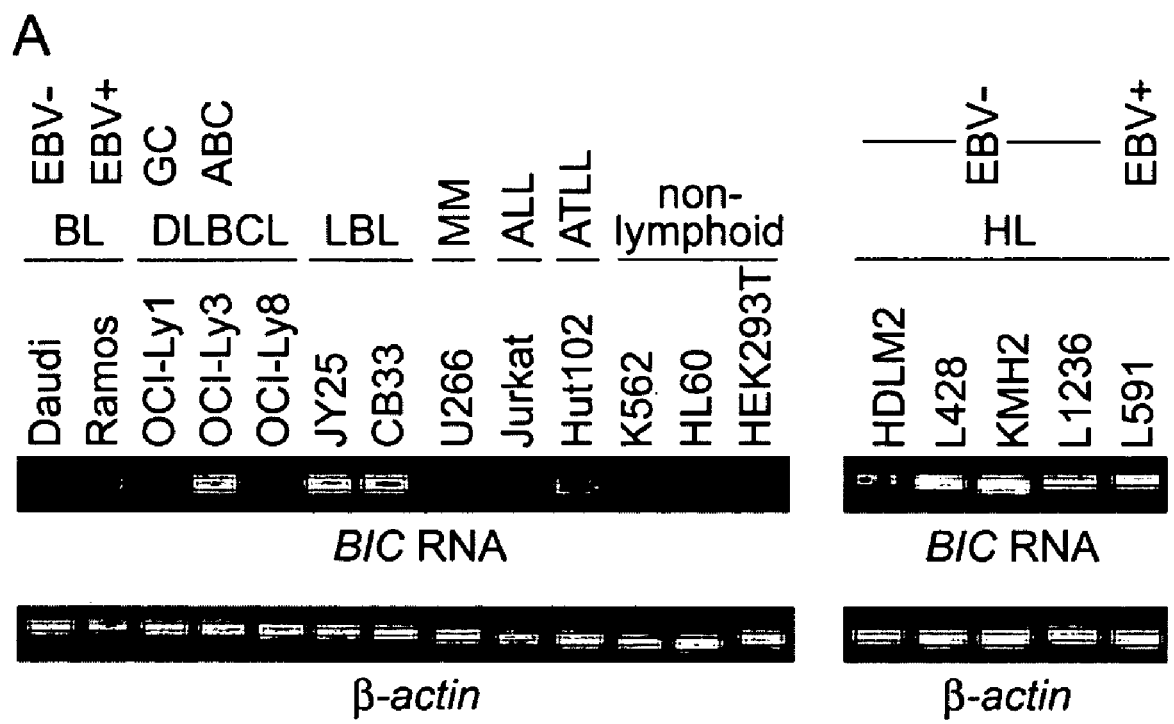
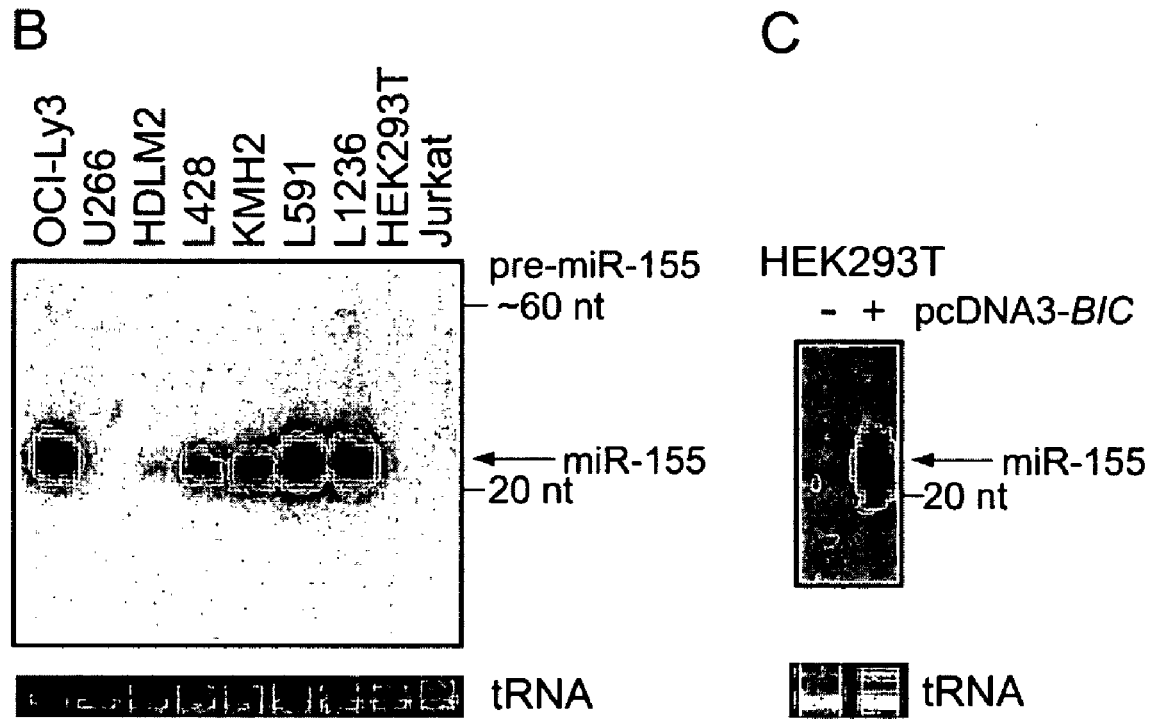

FIG. 4
A
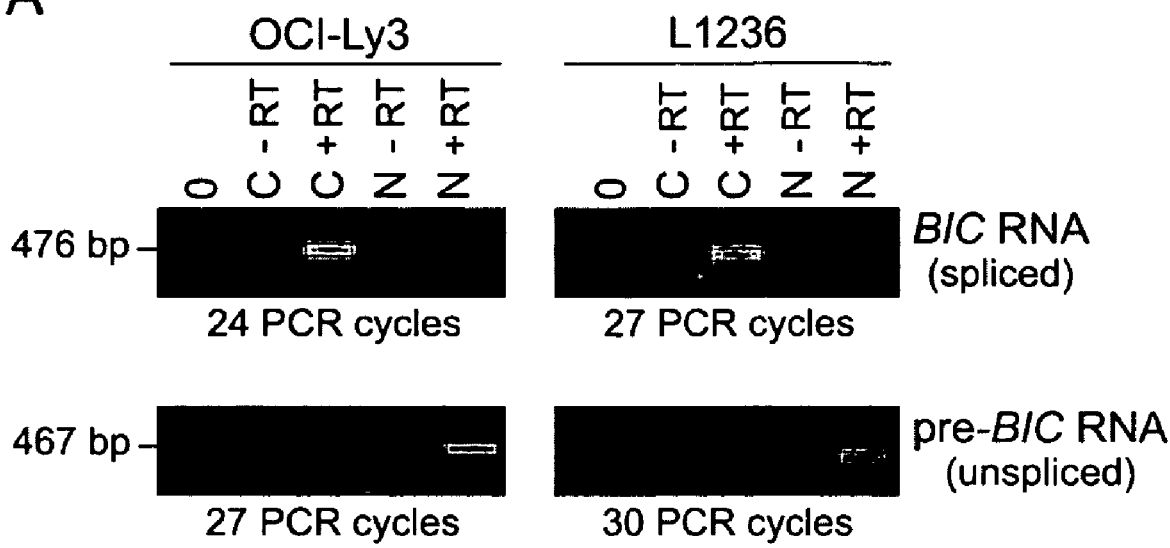
B
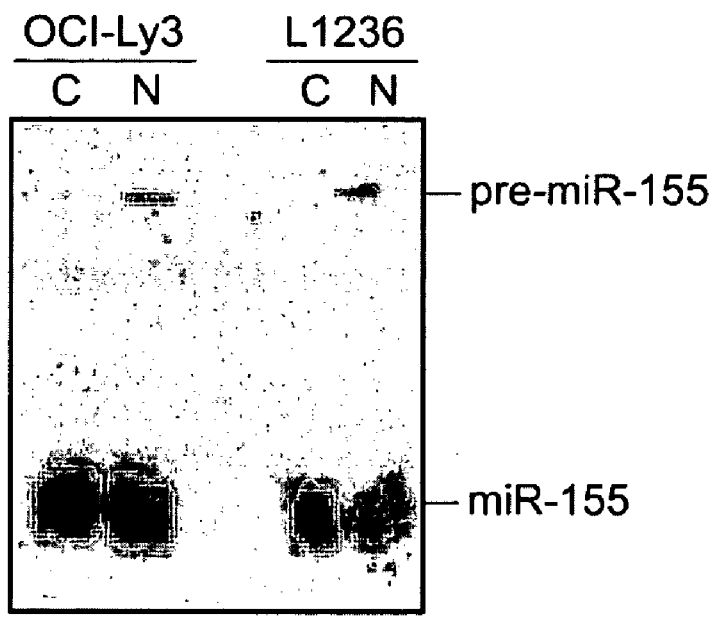

FIG. 8
A
miR-155 target: PU.1 transcription factor mRNA
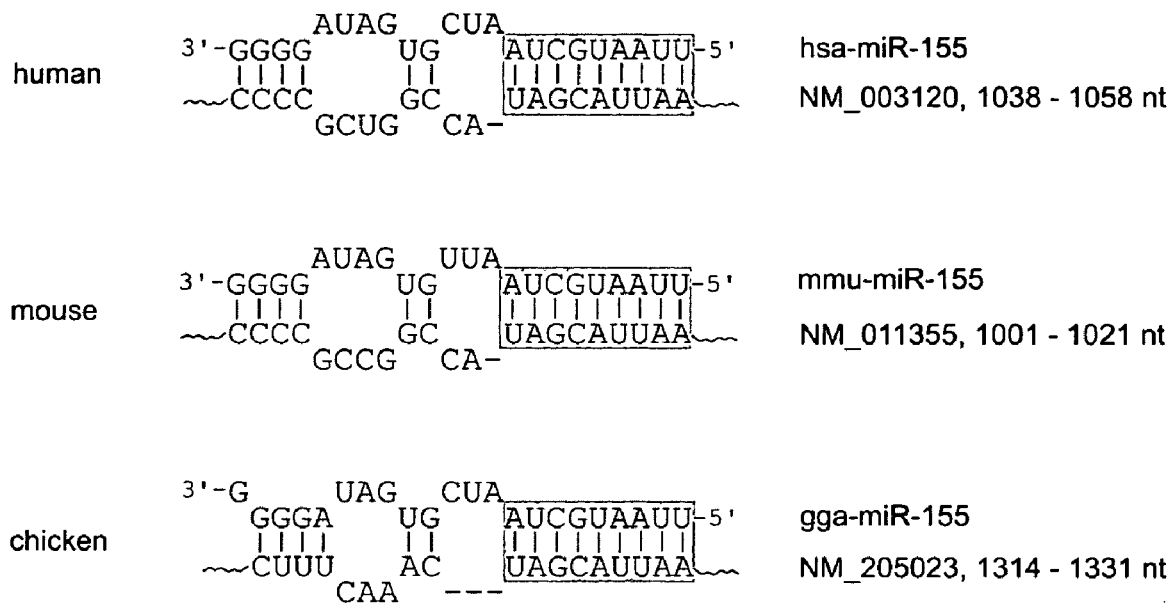
B
miR-155 target: CEBPB transcription factor mRNA
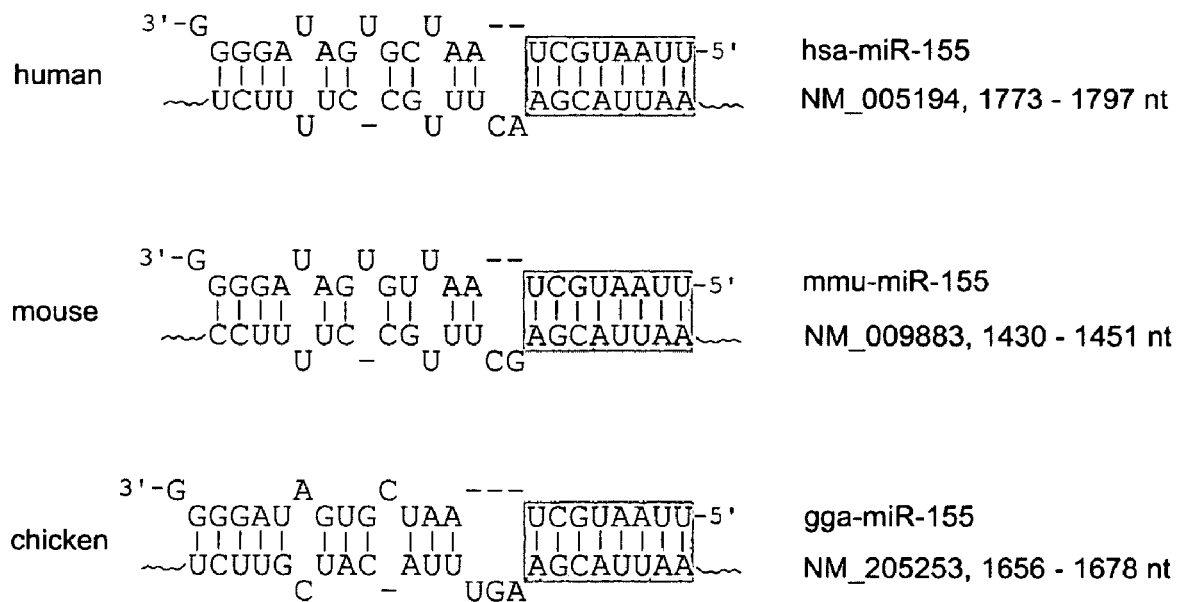

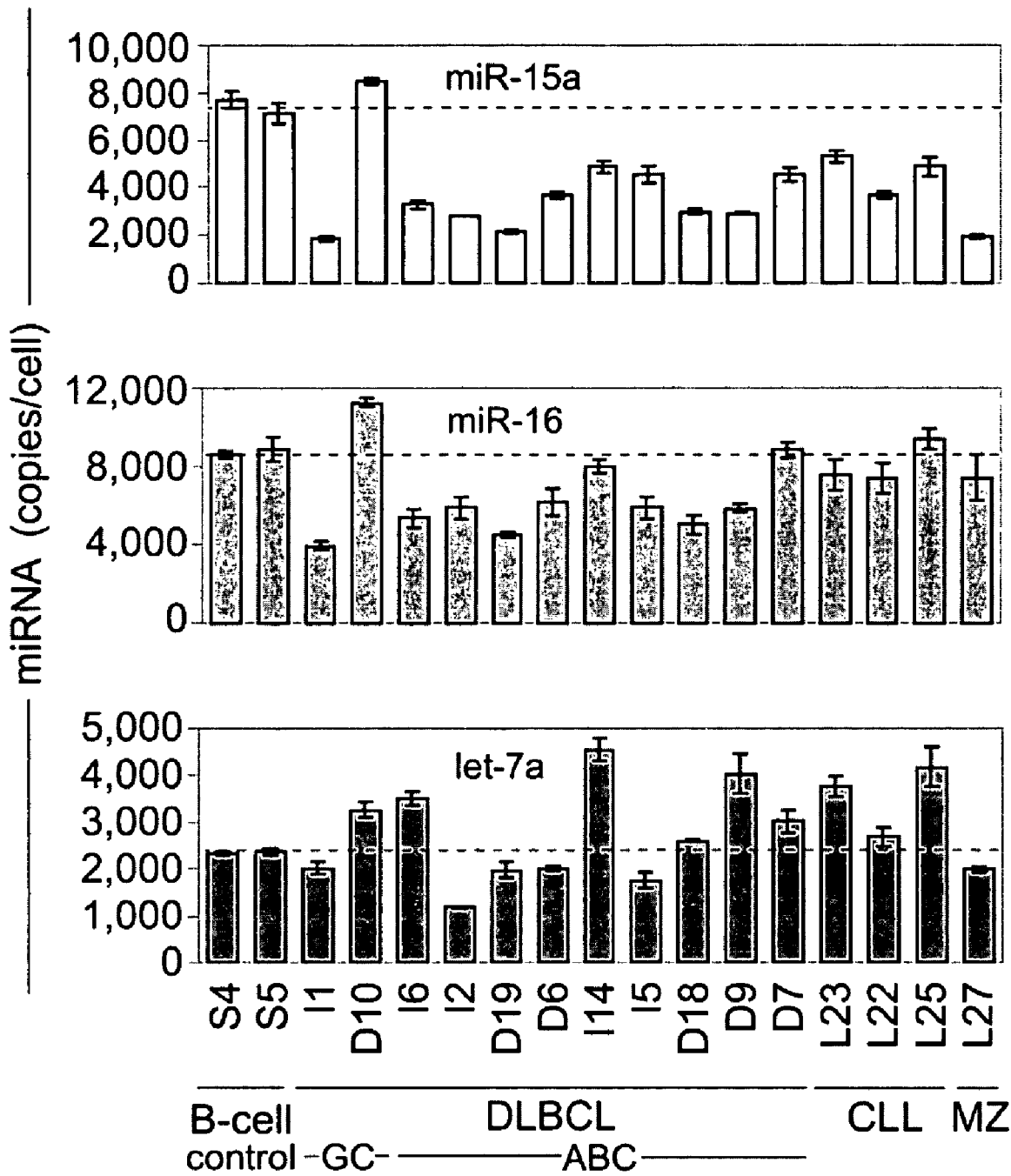

SEQUENCE LISTING

```
<160> NUMBER OF SEQ ID NOS: 51

<210> SEQ ID NO 1
<211> LENGTH: 27
<212> TYPE: DNA
<213> ORGANISM: Artificial
<220> FEATURE:
<223> OTHER INFORMATION: primer A, BIC RNA PCR primer

<400> SEQUENCE: 1
caagaacaac ctaccagaga ccttacc                                         27

<210> SEQ ID NO 2
<211> LENGTH: 24
<212> TYPE: DNA
<213> ORGANISM: Artificial
<220> FEATURE:
<223> OTHER INFORMATION: primer C, BIC RNA PCR primer

<400> SEQUENCE: 2
tgataaaaac aaacatgggt tgac                                            24

<210> SEQ ID NO 3
<211> LENGTH: 22
```

```
<212> TYPE: DNA
<213> ORGANISM: Artificial
<220> FEATURE:
<223> OTHER INFORMATION: b-actin PCR primer

<400> SEQUENCE: 3
ctgtgctatc cctgtacgcc tc                                              22

<210> SEQ ID NO 4
<211> LENGTH: 26
<212> TYPE: DNA
<213> ORGANISM: Artificial
<220> FEATURE:
<223> OTHER INFORMATION: b-actin PCR primer

<400> SEQUENCE: 4
catgatggag ttgaaggtag tttcgt                                          26

<210> SEQ ID NO 5
<211> LENGTH: 22
<212> TYPE: DNA
<213> ORGANISM: Artificial
<220> FEATURE:
<223> OTHER INFORMATION: miR-155 probe

<400> SEQUENCE: 5
cccctatcac gattagcatt aa                                              22

<210> SEQ ID NO 6
<211> LENGTH: 24
<212> TYPE: DNA
<213> ORGANISM: Artificial
<220> FEATURE:
<223> OTHER INFORMATION: primer B, BIC RNA PCR primer

<400> SEQUENCE: 6
ctgtcactcc agctttataa ccgc                                            24

<210> SEQ ID NO 7
<211> LENGTH: 20
<212> TYPE: DNA
<213> ORGANISM: Artificial
<220> FEATURE:
<223> OTHER INFORMATION: INVADER oligonucleotide

<400> SEQUENCE: 7
cccttcctgg tttgtgccaa                                                 20

<210> SEQ ID NO 8
<211> LENGTH: 23
<212> TYPE: DNA
<213> ORGANISM: Artificial
<220> FEATURE:
<223> OTHER INFORMATION: probe

<400> SEQUENCE: 8
ccgtcacgcc tcccattaga gcc                                             23

<210> SEQ ID NO 9
<211> LENGTH: 15
<212> TYPE: RNA
<213> ORGANISM: Artificial
<220> FEATURE:
<223> OTHER INFORMATION: stacking oligonucleotide
<220> FEATURE:
<221> NAME/KEY: modified_base
<222> LOCATION: (1)..(15)
```

```
<223> OTHER INFORMATION: 2'-O-methylated nucleotide

<400> SEQUENCE: 9
aucuccauug ggugg                                                    15

<210> SEQ ID NO 10
<211> LENGTH: 17
<212> TYPE: RNA
<213> ORGANISM: Artificial
<220> FEATURE:
<223> OTHER INFORMATION: arrestor oligonucleotide
<220> FEATURE:
<221> NAME/KEY: modified_base
<222> LOCATION: (1)..(17)
<223> OTHER INFORMATION: 2'-O-methylated nucleotide

<400> SEQUENCE: 10
ggcucuaaug ggaggcg                                                  17

<210> SEQ ID NO 11
<211> LENGTH: 27
<212> TYPE: DNA
<213> ORGANISM: Artificial
<220> FEATURE:
<223> OTHER INFORMATION: INVADER oligonucleotide

<400> SEQUENCE: 11
agaagtggaa aggtagattc tctgcta                                       27

<210> SEQ ID NO 12
<211> LENGTH: 21
<212> TYPE: DNA
<213> ORGANISM: Artificial
<220> FEATURE:
<223> OTHER INFORMATION: probe

<400> SEQUENCE: 12
ccgtcacgcc tccgcacaac c                                             21

<210> SEQ ID NO 13
<211> LENGTH: 17
<212> TYPE: RNA
<213> ORGANISM: Artificial
<220> FEATURE:
<223> OTHER INFORMATION: stacking oligonucleotide
<220> FEATURE:
<221> NAME/KEY: modified_base
<222> LOCATION: (1)..(17)
<223> OTHER INFORMATION: 2'-O-methylated nucleotide

<400> SEQUENCE: 13
guauuaugug gcuaagc                                                  17

<210> SEQ ID NO 14
<211> LENGTH: 15
<212> TYPE: RNA
<213> ORGANISM: Artificial
<220> FEATURE:
<223> OTHER INFORMATION: arrestor oligonucleotide
<220> FEATURE:
<221> NAME/KEY: modified_base
<222> LOCATION: (1)..(15)
<223> OTHER INFORMATION: 2'-O-methylated nucleotide

<400> SEQUENCE: 14
gguugugcgg aggcg                                                    15
```

```
<210> SEQ ID NO 15
<211> LENGTH: 21
<212> TYPE: DNA
<213> ORGANISM: Artificial
<220> FEATURE:
<223> OTHER INFORMATION: INVADER oligonucleotide
<220> FEATURE:
<221> NAME/KEY: modified_base
<222> LOCATION: (1)..(10)
<223> OTHER INFORMATION: 2'-O-methylated nucleotide

<400> SEQUENCE: 15
ggcuucggcc cccctatcac c                                              21

<210> SEQ ID NO 16
<211> LENGTH: 34
<212> TYPE: DNA
<213> ORGANISM: Artificial
<220> FEATURE:
<223> OTHER INFORMATION: probe
<220> FEATURE:
<221> NAME/KEY: modified_base
<222> LOCATION: (25)..(34)
<223> OTHER INFORMATION: 2'-O-methylated nucleotide

<400> SEQUENCE: 16
ccgtcgctgc gtgattagca ttaaggcuuc ggcc                                34

<210> SEQ ID NO 17
<211> LENGTH: 18
<212> TYPE: RNA
<213> ORGANISM: Artificial
<220> FEATURE:
<223> OTHER INFORMATION: arrestor oligonucleotide
<220> FEATURE:
<221> NAME/KEY: modified_base
<222> LOCATION: (1)..(18)
<223> OTHER INFORMATION: 2'-O-methylated nucleotide

<400> SEQUENCE: 17
uuaaugcuaa ucacgcag                                                  18

<210> SEQ ID NO 18
<211> LENGTH: 26
<212> TYPE: DNA
<213> ORGANISM: Artificial
<220> FEATURE:
<223> OTHER INFORMATION: INVADER oligonucleotide
<220> FEATURE:
<221> NAME/KEY: modified_base
<222> LOCATION: (1)..(14)
<223> OTHER INFORMATION: 2'-O-methylated nucleotide

<400> SEQUENCE: 18
ggcacuuuug ugcccacaaa ccattc                                         26

<210> SEQ ID NO 19
<211> LENGTH: 36
<212> TYPE: DNA
<213> ORGANISM: Artificial
<220> FEATURE:
<223> OTHER INFORMATION: probe
<220> FEATURE:
<221> NAME/KEY: modified_base
<222> LOCATION: (24)..(36)
<223> OTHER INFORMATION: 2'-O-methylated nucleotide

<400> SEQUENCE: 19
aacgaggcgc acatgtgctg ctacgaguuu ucgucg                              36
```

```
<210> SEQ ID NO 20
<211> LENGTH: 17
<212> TYPE: RNA
<213> ORGANISM: Artificial
<220> FEATURE:
<223> OTHER INFORMATION: arrestor oligonucleotide
<220> FEATURE:
<221> NAME/KEY: modified_base
<222> LOCATION: (1)..(17)
<223> OTHER INFORMATION: 2'-O-methylated nucleotide

<400> SEQUENCE: 20
uagcagcaca ugugcgc                                                  17

<210> SEQ ID NO 21
<211> LENGTH: 25
<212> TYPE: DNA
<213> ORGANISM: Artificial
<220> FEATURE:
<223> OTHER INFORMATION: INVADER oligonucleotide
<220> FEATURE:
<221> NAME/KEY: modified_base
<222> LOCATION: (1)..(14)
<223> OTHER INFORMATION: 2'-O-methylated nucleotide

<400> SEQUENCE: 21
ggcacuuuug ugcccgccaa tattg                                         25

<210> SEQ ID NO 22
<211> LENGTH: 37
<212> TYPE: DNA
<213> ORGANISM: Artificial
<220> FEATURE:
<223> OTHER INFORMATION: probe
<220> FEATURE:
<221> NAME/KEY: modified_base
<222> LOCATION: (25)..(37)
<223> OTHER INFORMATION: 2'-O-methylated nucleotide

<400> SEQUENCE: 22
aacgaggcgc actacgtgct gctacgaguu uucgucg                            37

<210> SEQ ID NO 23
<211> LENGTH: 18
<212> TYPE: RNA
<213> ORGANISM: Artificial
<220> FEATURE:
<223> OTHER INFORMATION: arrestor oligonucleotide
<220> FEATURE:
<221> NAME/KEY: modified_base
<222> LOCATION: (1)..(18)
<223> OTHER INFORMATION: 2'-O-methylated nucleotide

<400> SEQUENCE: 23
uagcagcacg uagugcgc                                                 18

<210> SEQ ID NO 24
<211> LENGTH: 26
<212> TYPE: DNA
<213> ORGANISM: Artificial
<220> FEATURE:
<223> OTHER INFORMATION: INVADER oligonucleotide
<220> FEATURE:
<221> NAME/KEY: modified_base
<222> LOCATION: (1)..(14)
<223> OTHER INFORMATION: 2'-O-methylated nucleotide

<400> SEQUENCE: 24
ggcacuuuug ugccaactat acaact                                        26
```

-continued

```
<210> SEQ ID NO 25
<211> LENGTH: 36
<212> TYPE: DNA
<213> ORGANISM: Artificial
<220> FEATURE:
<223> OTHER INFORMATION: probe
<220> FEATURE:
<221> NAME/KEY: modified_base
<222> LOCATION: (24)..(36)
<223> OTHER INFORMATION: 2'-O-methylated nucleotide

<400> SEQUENCE: 25
ccgtcgctgc gtctactacc tcacgaguuu ucgucg                          36

<210> SEQ ID NO 26
<211> LENGTH: 17
<212> TYPE: RNA
<213> ORGANISM: Artificial
<220> FEATURE:
<223> OTHER INFORMATION: arrestor oligonucleotide
<220> FEATURE:
<221> NAME/KEY: modified_base
<222> LOCATION: (1)..(17)
<223> OTHER INFORMATION: 2'-O-methylated nucleotide

<400> SEQUENCE: 26
ugagguagua gacgcag                                               17

<210> SEQ ID NO 27
<211> LENGTH: 22
<212> TYPE: DNA
<213> ORGANISM: Artificial
<220> FEATURE:
<223> OTHER INFORMATION: INVADER oligonucleotide

<400> SEQUENCE: 27
catccttgcg caggggccat ga                                         22

<210> SEQ ID NO 28
<211> LENGTH: 30
<212> TYPE: DNA
<213> ORGANISM: Artificial
<220> FEATURE:
<223> OTHER INFORMATION: probe

<400> SEQUENCE: 28
ccgccgagat cacctaatct tctgctgtat                                 30

<210> SEQ ID NO 29
<211> LENGTH: 22
<212> TYPE: RNA
<213> ORGANISM: Artificial
<220> FEATURE:
<223> OTHER INFORMATION: arrestor oligonucleotide
<220> FEATURE:
<221> NAME/KEY: modified_base
<222> LOCATION: (1)..(22)
<223> OTHER INFORMATION: 2'-O-methylated nucleotide

<400> SEQUENCE: 29
auacagagaa gauuagguga uc                                         22

<210> SEQ ID NO 30
<211> LENGTH: 10
<212> TYPE: DNA
<213> ORGANISM: Artificial
<220> FEATURE:
```

```
<223> OTHER INFORMATION: 3' portion of FRET oligonucleotide

<400> SEQUENCE: 30
tgcttcgtgg                                                              10

<210> SEQ ID NO 31
<211> LENGTH: 11
<212> TYPE: DNA
<213> ORGANISM: Artificial
<220> FEATURE:
<223> OTHER INFORMATION: 3' portion of FRET oligonucleotide

<400> SEQUENCE: 31
ttctcagtgc g                                                            11

<210> SEQ ID NO 32
<211> LENGTH: 27
<212> TYPE: DNA
<213> ORGANISM: Artificial
<220> FEATURE:
<223> OTHER INFORMATION: secondary reaction template
<220> FEATURE:
<221> NAME/KEY: modified_base
<222> LOCATION: (25)..(27)
<223> OTHER INFORMATION: 2'-O-methylated nucleotide

<400> SEQUENCE: 32
ccaggaagca tgtggtgcgc ctcguuu                                           27

<210> SEQ ID NO 33
<211> LENGTH: 27
<212> TYPE: DNA
<213> ORGANISM: Artificial
<220> FEATURE:
<223> OTHER INFORMATION: secondary reaction template
<220> FEATURE:
<221> NAME/KEY: modified_base
<222> LOCATION: (25)..(27)
<223> OTHER INFORMATION: 2'-O-methylated nucleotide

<400> SEQUENCE: 33
ccaggaagca tgtggaggcg tgacggu                                           27

<210> SEQ ID NO 34
<211> LENGTH: 27
<212> TYPE: DNA
<213> ORGANISM: Artificial
<220> FEATURE:
<223> OTHER INFORMATION: secondary reaction template
<220> FEATURE:
<221> NAME/KEY: modified_base
<222> LOCATION: (25)..(27)
<223> OTHER INFORMATION: 2'-O-methylated nucleotide

<400> SEQUENCE: 34
ccaggaagca tgtgacgcag cgacggu                                           27

<210> SEQ ID NO 35
<211> LENGTH: 29
<212> TYPE: DNA
<213> ORGANISM: Artificial
<220> FEATURE:
<223> OTHER INFORMATION: secondary reaction template
<220> FEATURE:
<221> NAME/KEY: modified_base
<222> LOCATION: (27)..(29)
<223> OTHER INFORMATION: 2'-O-methylated nucleotide

<400> SEQUENCE: 35
```
cgcagtgaga atgaggtgat ctcggcggu                                            29

<210> SEQ ID NO 36
<211> LENGTH: 37
<212> TYPE: DNA
<213> ORGANISM: Artificial
<220> FEATURE:
<223> OTHER INFORMATION: BIC RNA PCR primer

<400> SEQUENCE: 36
taatacgact cactataggg agcggagccc cgagccg                                   37

<210> SEQ ID NO 37
<211> LENGTH: 36
<212> TYPE: DNA
<213> ORGANISM: Artificial
<220> FEATURE:
<223> OTHER INFORMATION: BIC RNA PCR primer

<400> SEQUENCE: 37
ctcatgagat ttatttggtt acagtgaata acctgg                                    36

<210> SEQ ID NO 38
<211> LENGTH: 1488
<212> TYPE: DNA
<213> ORGANISM: Homo sapiens

<400> SEQUENCE: 38
cgcgggcttc ctgtgcgcgg ccgagcccgg gcccagcgcc gcctgcagcc tcgggaaggg          60
agcggatagc ggagccccga gccgcccgca gagcaagcgc ggggaaccaa ggagacgctc         120
ctggcactgc agataacttg tctgcatttc aagaacaacc taccagagac cttacctgtc        180
accttggctc tcccacccaa tggagatggc tctaatggtg gcacaaacca ggaaggggaa        240
atctgtggtt taaattcttt atgcctcatc ctctgagtgc tgaaggcttg ctgtaggctg        300
tatgctgtta atgctaatcg tgataggggt ttttgcctcc aactgactcc tacatattag        360
cattaacagt gtatgatgcc tgttactagc attcacatgg aacaaattgc tgccgtggga        420
ggatgacaaa gaagcatgag tcaccctgct ggataaactt agacttcagg ctttatcatt        480
tttcaatctg ttaatcataa tctggtcact gggatgttca accttaaact aagttttgaa        540
agtaaggtta tttaaaagat ttatcagtag tatcctaaat gcaaacattt tcatttaaat        600
gtcaagccca tgtttgtttt tatcattaac agaaaatata ttcatgtcat tcttaattgc        660
aggttttggc ttgttcatta taatgttcat aaacaccttt gattcaactg ttagaaatgt        720
gggctaaaca caaatttcta taatattttt gtagttaaaa attagaagga ctactaacct        780
ccagttatat catggattgt ctggcaacgt tttttaaaag atttagaaac tggtactttc        840
ccccaggtaa cgattttctg ttcaggcaac ttcagtttaa aattaatact tttatttgac        900
tcttaaaggg aaactgaaag gctatgaagc tgaattttt taatgaaata ttttttaacag       960 ttagcagggt aaataacatc tgacagctaa tgagatattt tttccataca agataaaaag       1020
atttaatcaa aaatttcata tttgaaatga agtcccaaat ctaggttcaa gttcaatagc       1080
ttagccacat aatacggttg tgcgagcaga gaatctacct ttccacttct aagcctgttt       1140
cttcctccat aaaatgggga taatacttta caaggttgtt gtgaggctta gatgagatag       1200
agaattattc cataagataa tcaagtgcta cattaatgtt atagttagat taatccaaga       1260
actagtcacc ctactttatt agagaagaga aaagctaatg atttgatttg cagaatattt       1320

```
aaggtttgga tttctatgca gtttttctaa ataaccatca cttacaaata tgtaaccaaa    1380
cgtaattgtt agtatattta atgtaaactt gttttaacaa ctcttctcaa cattttgtcc    1440
aggttattca ctgtaaccaa ataaatctca tgagtcttta gttgattt                 1488

<210> SEQ ID NO 39
<211> LENGTH: 24
<212> TYPE: DNA
<213> ORGANISM: Artificial
<220> FEATURE:
<223> OTHER INFORMATION: human BIC cDNA, intron 2

<400> SEQUENCE: 39
ctgtcactcc agctttataa ccgc                                           24

<210> SEQ ID NO 40
<211> LENGTH: 83
<212> TYPE: RNA
<213> ORGANISM: Homo sapiens

<400> SEQUENCE: 40
uuaaugcuaa ucgugauagg gguuuuugcc uccaacugac uccuacauau uagcauuaac    60
auuaaugcua aucgugauag ggg                                            83

<210> SEQ ID NO 41
<211> LENGTH: 22
<212> TYPE: RNA
<213> ORGANISM: Homo sapiens

<400> SEQUENCE: 41
uuaaugcuaa ucgugauagg gg                                             22

<210> SEQ ID NO 42
<211> LENGTH: 21
<212> TYPE: DNA
<213> ORGANISM: Artificial
<220> FEATURE:
<223> OTHER INFORMATION: INVADER Oligonucleotide

<400> SEQUENCE: 42
gccuucggcc cccctatcac c                                              21

<210> SEQ ID NO 43
<211> LENGTH: 65
<212> TYPE: RNA
<213> ORGANISM: Artificial
<220> FEATURE:
<223> OTHER INFORMATION: residues 305-370 of BIC RNA

<400> SEQUENCE: 43
cuguuaaugc uaaucgugau aggguuuuu gccuccaacu gacuccuaca uauuagcauu    60
aacag                                                                65

<210> SEQ ID NO 44
<211> LENGTH: 22
<212> TYPE: RNA
<213> ORGANISM: Mus musculus

<400> SEQUENCE: 44
uuaaugcuaa uugugauagg gg                                             22

<210> SEQ ID NO 45
<211> LENGTH: 22
```

```
<212> TYPE: RNA
<213> ORGANISM: Gallus gallus

<400> SEQUENCE: 45
uuaaugcuaa ucgugauagg gg                                              22

<210> SEQ ID NO 46
<211> LENGTH: 21
<212> TYPE: RNA
<213> ORGANISM: Artificial
<220> FEATURE:
<223> OTHER INFORMATION: residues 1038-1058 of NM_003120

<400> SEQUENCE: 46
ccccgcuggc cauagcauua a                                               21

<210> SEQ ID NO 47
<211> LENGTH: 21
<212> TYPE: RNA
<213> ORGANISM: Artificial
<220> FEATURE:
<223> OTHER INFORMATION: residues 1001-1021 of NM-011355

<400> SEQUENCE: 47
ccccgccggc cauagcauua a                                               21

<210> SEQ ID NO 48
<211> LENGTH: 18
<212> TYPE: RNA
<213> ORGANISM: Artificial
<220> FEATURE:
<223> OTHER INFORMATION: residues 1314-1331 of NM_205023

<400> SEQUENCE: 48
cuuucaaacu agcauuaa                                                   18

<210> SEQ ID NO 49
<211> LENGTH: 22
<212> TYPE: RNA
<213> ORGANISM: Artificial
<220> FEATURE:
<223> OTHER INFORMATION: residues 1773-1797 of NM_00519

<400> SEQUENCE: 49
ucuuuuccgu uucaagcauu aa                                              22

<210> SEQ ID NO 50
<211> LENGTH: 22
<212> TYPE: RNA
<213> ORGANISM: Artificial
<220> FEATURE:
<223> OTHER INFORMATION: residues 1430-1451 of NM-009883

<400> SEQUENCE: 50
ccuuuuccgu uucgagcauu aa                                              22

<210> SEQ ID NO 51
<211> LENGTH: 23
<212> TYPE: RNA
<213> ORGANISM: Artificial
<220> FEATURE:
<223> OTHER INFORMATION: residues 1656-1678 of NM_205253

<400> SEQUENCE: 51
ucuugcuaca uuugaagcau uaa                                             23
```

US 7,700,288 B2

MIR-155 ASSAY

This application claims the benefit of priority from U.S. Provisional Patent Application Nos. 60/652,301, filed on Feb. 11, 2005, and 60/656,245, filed Feb. 25, 2005, the disclosure of each of which is explicitly incorporated by reference herein.

ACKNOWLEDGEMENT OF FEDERAL RESEARCH SUPPORT

This invention was made, at least in part, with funding from the National Institutes of Health, Grant No. GM-30220. Accordingly, the United States Government may have certain rights in this invention.

BACKGROUND OF THE INVENTION

1. Field of the Invention

The invention relates to methods for diagnosing B-cell lymphoma in an animal. In particular, the invention relates to methods for distinguishing an animal having diffuse large B-cell lymphoma (DLBCL) with an activated B-cell (ABC) phenotype from an animal having DLBCL with a non-activated germinal-center (GC) phenotype. The invention also relates to methods for identifying compounds for treating B-cell lymphoma. The invention further relates to reagents and methods for determining the amount of miR-155 in sample isolated from an animal. In this regard, the invention relates to a set of oligonucleotides for determining the amount of miR-155 in sample isolated from an animal.

2. Background of the Invention

Inappropriate expression of proto-oncogenes or inactivation of tumor supressor genes can contribute to cancer. One example is the BIC gene, which was originally identified as a common site for insertion of pro-viral DNA in avian leukosis virus (ALV)-induced lymphomas (Tam et al., 1997, *Mol. Cell. Biol.* 17:1490-502; Clurman et al., 1989, *Mol. Cell. Biol.* 9:2657-64). Activation of the BIC gene can accelerate the pathogenesis of lymphomas and leukemias that are associated with up-regulation of c-MYC, showing that BIC functions in the etiology of these diseases (Tam et al., 2002, *J. Virol.* 76:4275-86). Expression of BIC RNA is low in normal lymphoid tissues, but elevated in Hodgkin and children's Burkitt lymphoma and in in vitro activated B- and T-cells (Haasch et al., 2002, *Cell. Immunol.* 217:78-86; Metzler et al., 2004, *Genes Chromosomes Cancer* 39:167-69; van den Berg et al., *Genes Chromosomes Cancer* 37:20-28).

Avian, murine, and human BIC RNA is a spliced and polyadenylated transcript that is approximately 1.7 kb in length (including the poly A tail) and is presumably generated by RNA polymerase II. Because BIC transcripts lack long open reading frames (ORFs), and their short, putative ORFs are not conserved, it has been suggested that BIC RNA functions as a non-protein-coding RNA (Tam, 2001, *Gene* 274: 157-67). Recently, a mouse microRNA (miRNA) molecule, designated miR-155 (Lagos-Quintana et al., 2002, *Curr. Biol.* 12:735-39), was found to be encoded within the only phylogenetically conserved region of BIC RNA (Id.). Typically, miRNAs are ~22 nucleotide long molecules that function in post-transcriptional down-regulation of gene expression in plants, vertebrates, and invertebrates (Bartel, 2004, *Cell* 116: 281-97; He et al., 2004, *Nat. Rev. Genet.* 5:522-31; Pasquinelli, 2002, *Trends Genet.* 18:171-73). Thus, miR-155 could be responsible for the oncogenic activity attributed to BIC RNA, inter alia, by down-regulating tumor suppressor gene transcription.

In animal cells, endogenous miRNAs are produced from primary RNA polymerase II transcripts (i.e., pri-miRNAs) by sequential processing in the nucleus and cytoplasm (Cullen, 2004, *Mol. Cell.* 16:861-65). Nuclear precursor RNAs are cleaved by the endonuclease Drosha in a "microprocessor complex," releasing pre-miRNAs, which are short 60-70 nucleotide imperfect hairpin structures. After transport to the cytoplasm by exportin-5, pre-miRNAs are processed by the endonuclease DICER, generating ~22 nucleotide duplexes, one strand of which is the mature miRNA. The conserved region of BIC RNA encoding miR-155 can form an imperfect hairpin structure (Tam, 2001, supra), suggesting that miR-155 is generated by this pathway (FIG. 1).

Changes in the levels of miRNAs may alter control of growth or apoptosis in some cancers (McManus, 2003, *Semin. Cancer Biol.* 13:253-58; Xu et al., 2004, *Trends Genet.* 20:617-24). Reductions in the levels of miR-15a plus miR-16, let-7a, and miR-143 plus miR-145 have been reported in chronic lymphocytic leukemia (CLL) (Calin et al., 2002, *Proc. Natl. Acad. Sci. U.S.A.* 99:15524-29), lung cancer (Takamizawa et al., 2004, *Cancer Res.* 64:3753-56), and colon carcinoma (Michael et al., 2003, *Mol. Cancer Res.* 1:882-91), respectively. Although BIC RNA is up-regulated in some human lymphomas (Metzler et al., 2004, supra; van den Berg et al., 2003, supra), very little is known about the levels of miR-155 in these cancers.

Diffuse large B-cell lymphoma (DLBCL), an aggressive B-cell neoplasm accounting for 30-40% of all lymphoma cases (The Non-Hodgkin's Lymphoma Classification Project, 1997, *Blood* 89:3909-18), can be categorized immunohistochemically into groups with significantly different clinical outcomes (Chang et al., 2004, *Am. J. Surg. Pathol.* 28:464-70). The prognosis is poorer for patients having DLBCL with an activated B-cell (ABC) phenotype than a non-activated germinal-center (GC) phenotype. So far, a relationship has not been examined between miR-155 and BIC RNA levels and the phenotypes of this most frequent of all lymphoid neoplasms.

Thus, there is a need in the art for methods for diagnosing B-cell lymphoma in patients. In addition, there is a need in the art for methods for distinguishing individuals having DLBCL with an ABC phenotype from individuals having DLBCL with a GC phenotype. Such methods would be particularly useful in situations where conventional histologic and immunophenotypic methods cannot provide an accurate diagnosis of B-cell lymphoma, and in particular, DLBCL with an ABC phenotype. Such methods would also be useful in determining suitable courses of therapy for treating patients having B-cell lymphoma, and in particular, DLBCL with an ABC phenotype. Therefore, the development of such diagnostic methods would have wide application in the medical arts.

SUMMARY OF THE INVENTION

The present invention provides methods for diagnosing B-cell lymphoma in an animal comprising the step of assaying a B-cell sample isolated from the animal to determine the amount of miR-155 in the sample, and diagnosing B-cell lymphoma in the animal if the amount of miR-155 in the B-cell sample is higher than the amount of miR-155 in normal B-cells.

The present invention also provides methods for diagnosing B-cell lymphoma in an animal comprising determining the amount of miR-155 in a B-cell sample isolated from the animal; determining the amount of miR-155 in normal B-cells or evaluating a range of average amounts of miR-155 in B-cells from a plurality of normal individuals; and diagnosing B-cell lymphoma in the animal if the amount of miR-155 in the B-cell sample isolated from the animal is higher than the amount of miR-155 in the normal B-cells.

The present invention also provides methods for diagnosing diffuse large B-cell lymphoma (DLBCL) with an activated B-cell (ABC) phenotype in an animal comprising the step of assaying a B-cell sample isolated from the animal to determine the amount of miR-155 in the sample, and diagnosing DLBCL with an ABC phenotype in the animal if the amount of miR-155 in the B-cell sample is higher than the amount of miR-155 in a sample of DLBCL cells with a GC phenotype.

The present invention also provides methods for diagnosing diffuse large B-cell lymphoma (DLBCL) with an activated B-cell (ABC) phenotype in a animal comprising determining the amount of miR-155 in a B-cell sample isolated from the animal; determining the amount of miR-155 in a sample of DLBCL cells with a non-activated germinal-center (GC) phenotype; and diagnosing DLBCL with an ABC phenotype in the animal if the amount of miR-155 in the B-cell sample isolated from the animal is higher than the amount of miR-155 in the sample of DLBCL cells with a GC phenotype.

The present invention also provides methods for identifying a compound for treating B-cell lymphoma comprising determining the amount of miR-155 in a B-cell lymphoma sample; exposing the B-cell lymphoma sample to the compound; determining the amount of miR-155 in the B-cell lymphoma sample following exposure of the B-cell lymphoma sample to the compound; and identifying a compound for treating B-cell lymphoma if the amount of miR-155 in the B-cell lymphoma sample before exposure to the compound is higher than the amount of miR-155 in the B-cell lymphoma sample after exposure to the compound.

The present invention also provides reagents for determining the amount of miR-155 in sample isolated from an animal. In particular, the present invention provides a set of oligonucleotides for determining the amount of miR-155 in sample isolated from an animal comprising an invasive cleavage oligonucleotide having the nucleotide sequence set forth in SEQ ID NO: 15; a probe having the nucleotide sequence set forth in SEQ ID NO: 16; and an arrestor oligonucleotide having the nucleotide sequence set forth in SEQ ID NO: 17.

Specific preferred embodiments of the present invention will become evident from the following more detailed description of certain preferred embodiments and the claims.

BRIEF DESCRIPTION OF THE DRAWINGS

FIGS. 2A-2B show (2A) the nucleotide sequence of human BIC cDNA (SEQ ID NO: 38), wherein the 5' end of BIC RNA corresponds to position 1 (Tam, 2001, supra), the locations and sizes of the introns present in the primary transcript are as indicated (intron 2, SEQ ID NO: 39), the region corresponding to mature miR-155 begins at position 308 and is indicated by a dotted line, the arrows designated A, B, and C denote oligonucleotide primers used in RT-PCR assays, the shaded nucleotides at positions 196-237 and 1019-1070 (for BIC RNA) and positions 308-329 (for miR-155) represent sequences detected in Invader® assays, the polyadenylation signals which generate BIC RNA isoforms (Id.) are indicated in bold italics, the open arrows denote the ends of the BIC exon 3 sequence cloned into pcDNA3.BIC (see Example 2); and (2B) the sequence (SEQ ID NO: 40) and predicted secondary structure of pre-miR-155, wherein the sequence of mature miR-155 (SEQ ID NO: 41) is indicated in bold.

FIGS. 3A-3C show the results of (3A) semi-quantitative RT-PCR analysis of human lymphoid and non-lymphoid cell lines using primers specific for BIC RNA, (3B) Northern blot analysis of human lymphoid and non-lymphoid cell lines using a probe specific for miR-155, and (3C) Northern blot analysis of HEK293T cells transfected with the vector pcDNA3.BIC using a probe specific for miR-155 (BL=Burkitt lymphoma, DLBCL=diffuse large B-cell lymphoma, LBL=EBV-immortalized lymphoblastoid cell line, MM=multiple myeloma, ALL=acute lymphoblastic leukemia, ATLL=adult T-cell leukemia/lymphoma (HTLV+), HL=Hodgkin lymphoma, GC=germinal center-cell like, ABC=activated B-cell-like).

FIGS. 4A-4B show the results of (4A) RT-PCR analysis of nuclear and cytoplasmic RNA from OCI-Ly3 and L1236 cells using primers specific for spliced and unspliced BIC RNA, and (4B) Northern blot analysis of nuclear and cytoplasmic RNA from OCI-Ly3 and L1236 cells using a probe specific for miR-155 (N=nuclear, C=cytoplasmic, +RT=PCR performed with reverse transcriptase, −RT=PCR performed without reverse transcriptase, 0=PCR performed in the absence of template).

FIG. 8 shows potential targets of miR-155 binding in the 3' UTR conserved sequences of PU.1 mRNA (top panel) and C/EBP/β mRNA (bottom panel) from human, mouse, and chicken; both PU.1 mRNA and C/EBP/β mRNA encode developmentally regulated transcription factors (John et al., 2004, *PLos Biol.* 2:e363; Lewis et al., 2005, *Cell* 120:15-20); Sequences: hsa-miR-155 (SEQ ID NO: 41), mmu-miR-155 (SEQ ID NO: 44), gga-miR-155 (SEQ ID NO: 45), NM_003120 (SEQ ID NO: 46), NM-011355 (SEQ ID NO: 47), NM_205023 (SEQ ID NO: 48), NM_005194 (SEQ ID NO: 49), NM_009883 (SEQ ID NO: 50), NM_205253 (SEQ ID NO: 51).

FIG. 10 shows the levels of miR-15a, miR-16, and let-7a miRNA in normal B-cells (samples S4 and S5) and clinical B-cell lymphoma isolates as determined in Invader® miRNA assays, wherein error bars represent one standard deviation.

DETAILED DESCRIPTION OF THE INVENTION

Figure 1:
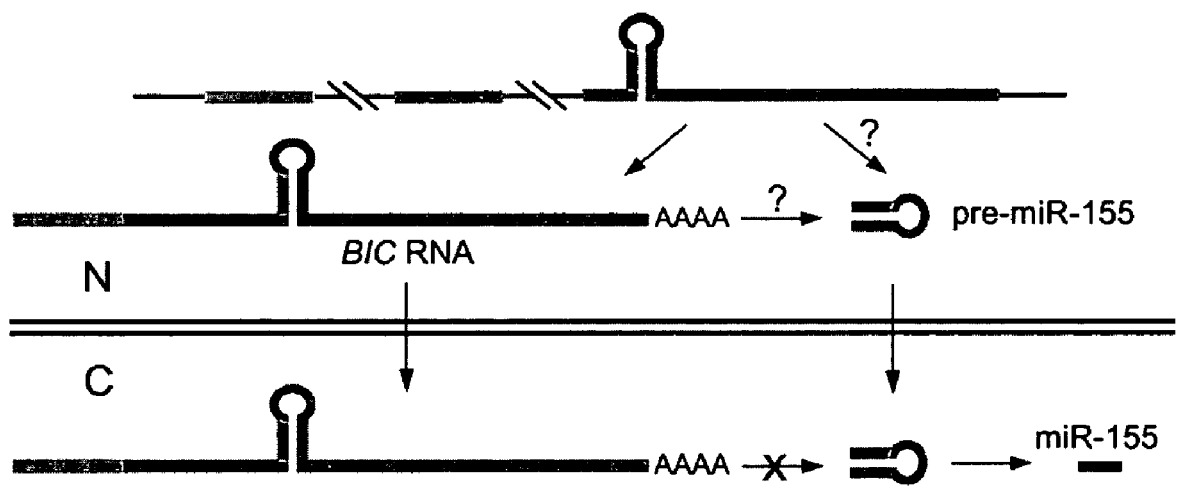
FIG. 1 shows a schematic representation of miR-155 production, in which pre-miR-155 is generated by the nuclear Drosha-containing microprocessor complex acting on the primary BIC gene transcript or on spliced and polyadenylated BIC RNA that has not yet been exported from the nucleus. This diagram also shows that spliced, polyadenylated BIC RNA that has been exported to the cytoplasm before being processed to pre-miR-155 cannot thereafter be processed to pre-miR-155, because the nuclear Drosha-containing microprocessor complex does not have access to cytoplasmic BIC RNA.

The invention provides methods for diagnosing B-cell lymphoma in an animal. In particular, the invention provides methods for distinguishing an animal having diffuse large B-cell lymphoma (DLBCL) with an activated B-cell (ABC) phenotype from an animal having DLBCL with a non-activated germinal-center (GC) phenotype. The invention also provides methods for identifying compounds for treating B-cell lymphoma. The invention further provides reagents and methods for determining the amount of miR-155 in sample isolated from an animal. In this regard, the invention provides a set of oligonucleotides for determining the amount of miR-155 in sample isolated from an animal.

Recombinant nucleic acid methods used herein are generally those set forth in Sambrook et al., *Molecular Cloning. A Laboratory Manual* (Cold Spring Harbor Laboratory Press, 1989) or *Current Protocols in Molecular Biology* (Ausubel et al., eds., Green Publishers Inc. and Wiley and Sons 1994).

In one embodiment of the invention, B-cell lymphoma is diagnosed in an animal by assaying a B-cell sample isolated from the animal to determine the amount of miR-155 in the sample, and diagnosing B-cell lymphoma in the animal if the amount of miR-155 in the B-cell sample is higher than the amount of miR-155 in normal B-cells.

In another embodiment of the invention, B-cell lymphoma is diagnosed in an animal by determining the amount of miR-155 in a B-cell sample isolated from the animal; determining the amount of miR-155 in normal B-cells; and diagnosing B-cell lymphoma in the animal if the amount of miR-155 in the B-cell sample isolated from the animal is higher than the amount of miR-155 in the normal B-cells.

In preferred embodiments of the invention, the B-cell lymphoma being diagnosed in the animal is diffuse large B-cell lymphoma (DLBCL), chronic lymphocytic leukemia (CLL), or marginal zone (MZ) B-cell lymphoma.

In preferred embodiments of the invention, the animal being diagnosed is a mammal, and even more preferably, the animal being diagnosed is a human.

In the methods of the invention, the amount of miR-155 in a given sample may be determined using any suitable procedure for quantitating RNA known to those of skill in the art, including, but not limited to, polymerase chain reaction (PCR), ligase chain reaction (LCR), self-sustained sequence replication system (Guatelli et al., 1990, *Proc. Natl. Acad. Sci. U.S.A.* 87:1874-78), Q-beta replicase method, Northern blot assay, RNase protection assay, cycling probe reaction (Duck et al., 1990, *Biotechniques* 9:142-48), and branched DNA (bDNA) method (Urdea et al., 1987, *Gene* 61:253-64). In preferred embodiments of the invention, invasive cleavage reactions (U.S. Pat. No. 6,692,917; Eis et al., 2001, supra; and U.S. Patent Application Publication Nos. 2003/0104378 and US 2003/0186238)—such as those sold under the trademark Invader®—are used to determine the amount of miR-155 in a given sample.

In one method of the invention, normal (or control) B-cells may be obtained from a healthy individual. In another method of the invention, normal (or control) B-cells may be obtained from a cultured cell line, provided that the cultured cell line expresses an amount of miR-155 that is comparable to that expressed by B-cells isolated from a healthy individual. In one method of the invention, the amount of miR-155 in normal B-cells is determined by referring to a reference standard for the amount of miR-155 expression for normal B-cells (for example, compiled from a plurality of normal individual B-cell samples), or that is otherwise known or can be readily determined by those of skill in the art.

In a preferred embodiment of the invention, the diagnosis of B-cell lymphoma is based on an observation that the amount of miR-155 in the B-cell sample isolated from the animal is at least two times higher than the amount of miR-155 in the normal B-cells. In other preferred embodiments, the diagnosis of B-cell lymphoma is based on an observation that the amount of miR-155 in the B-cell sample isolated from the animal is at least five times higher than the amount of miR-155 in the normal B-cells, or at least ten times higher than the amount of miR-155 in the normal B-cells, or at least fifteen times higher than the amount of miR-155 in the normal B-cells, or at least twenty times higher than the amount of miR-155 in the normal B-cells, or at least thirty times higher than the amount of miR-155 in the normal B-cells.

In another embodiment of the invention, diffuse large B-cell lymphoma (DLBCL) with an activated B-cell (ABC) phenotype is diagnosed in an animal by assaying a B-cell sample isolated from the animal to determine the amount of miR-155 in the sample, and diagnosing DLBCL with an ABC phenotype in the animal if the amount of miR-155 in the B-cell sample is higher than the amount of miR-155 in a sample of DLBCL cells with a GC phenotype.

In another embodiment of the invention, diffuse large B-cell lymphoma (DLBCL) with an activated B-cell (ABC) phenotype is diagnosed in a animal by determining the amount of miR-155 in a B-cell sample isolated from the animal; determining the amount of miR-155 in a sample of DLBCL cells with a non-activated germinal-center (GC) phenotype; and diagnosing DLBCL with an ABC phenotype in the animal if the amount of miR-155 in the B-cell sample isolated from the animal is higher than the amount of miR-155 in the sample of DLBCL cells with a GC phenotype.

In one method of the invention, DLBCL cells with a GC phenotype are obtained from a cultured cell line, or from a reference standard amount of miR-155 determined from a plurality of samples of one or a plurality of cultured cell lines, or from one or a plurality of DLBCL/GC clinical samples.

In another method of the invention, the amount of miR-155 in normal B-cells is determined by referring to a reference standard for the amount of miR-155 expression for normal B-cells (for example, compiled from a plurality of normal individual B-cell samples), or that is otherwise known or can be readily determined by those of skill in the art.

In a preferred embodiment of the invention, the diagnosis of DLBCL cells with an ABC phenotype is based on an observation that the amount of miR-155 in the B-cell sample isolated from the animal is at least two times higher than the amount of miR-155 in the sample of DLBCL cells with a GC phenotype.

In another embodiment of the invention, a compound for treating B-cell lymphoma is identified by determining the amount of miR-155 in a B-cell lymphoma sample; exposing the B-cell lymphoma sample to the compound; determining the amount of miR-155 in the B-cell lymphoma sample following exposure of the B-cell lymphoma sample to the compound; and identifying a compound for treating B-cell lymphoma if the amount of miR-155 in the B-cell lymphoma sample before exposure to the compound is higher than the amount of miR-155 in the B-cell lymphoma sample after exposure to the compound.

In one method of the invention, the B-cell lymphoma sample is obtained from a cultured cell line, or from one or a plurality of clinical samples.

In a preferred embodiment of the invention, the identification of a suitable compound for treating B-cell lymphoma is based on an observation that the amount of miR-155 in the B-cell lymphoma sample before exposure to the compound is at least two times higher than the amount of miR-155 in the B-cell lymphoma sample after exposure to the compound. In other preferred embodiments, the identification of a suitable compound for treating B-cell lymphoma is based on an observation that the amount of miR-155 in the B-cell lymphoma sample before exposure is at least five times higher than the amount of miR-155 in the B-cell lymphoma sample after exposure to the compound, or at least ten times higher than the amount of miR-155 in the B-cell lymphoma sample after exposure to the compound, or at least fifteen times higher than the amount of miR-155 in the B-cell lymphoma sample after exposure to the compound, or at least twenty times higher than the amount of miR-155 in the B-cell lymphoma sample after exposure to the compound, or at least thirty times higher than the amount of miR-155 in the B-cell lymphoma sample after exposure to the compound.

The invention also provides reagents for determining the amount of miR-155 in sample isolated from an animal. In one embodiment of the invention, a set of oligonucleotides is provided for determining the amount of miR-155 in sample isolated from an animal, comprising an invasive cleavage oligonucleotide having the nucleotide sequence set forth in SEQ ID NO: 15; a probe having the nucleotide sequence set forth in SEQ ID NO: 16; and an arrestor oligonucleotide having the nucleotide sequence set forth in SEQ ID NO: 17.

The Examples that follow are illustrative of specific embodiments of the invention, and various uses thereof. They are set forth for explanatory purposes only, and are not to be taken as limiting the invention.

Example 1

Analysis of BIC RNA and miR-155 Levels in Activated Lymphoid Cells

BIC RNA and miR-155 levels in a number of human lymphoid and non-lymphoid cell lines were determined by semi-quantitative reverse transcriptase PCR (RT-PCR) and Northern blotting, respectively. Total RNA was isolated from cultured cells using Trizol (Invitrogen; Carlsbad, Calif.), and RNA integrity was monitored by electrophoresis on 8% denaturing polyacrylamide gels. Nuclear and cytoplasmic RNA were isolated according to standard protocols (Sambrook et al., 1989, supra). In particular, nuclear RNA was isolated by adding Trizol directly to nuclear pellets (Chomczynski et al., 1987, *Anal. Biochem.* 162:156-59). Semi-quantitative RT-PCR was performed by first using the Superscript First-Strand Synthesis System (Invitrogen) to reverse transcribe 2 µg of DNase I-treated total RNA in a total volume of 20 µL. One tenth of the reverse transcriptase reaction mixture was then amplified by PCR using either BIC RNA-specific primers (primer A, 5'-CAAGA-ACAAC-CTACC-AGAGA-CCTTA-CC-3', SEQ ID NO: 1; primer C, 5'-TGATA-AAAAC-AAACA-TGGGC-TTGAC-3'; SEQ ID NO: 2; FIG. 2) or control primers specific for β-actin (5'-CTGTG-CTATC-CCTGT-ACGCC-TC-3', SEQ ID NO: 3; 5'-CATGA-TGGAG-TTGAA-GGTAG-TTTCG-T-3', SEQ ID NO: 4) and an annealing temperature of 58° C. Reactions containing BIC RNA primers were amplified for 30 cycles and reactions containing β-action primers were amplified for 24 cycles. Amplification products were verified to be in the linear range by analyzing products generated at different cycle numbers on 2% agarose gels. Northern blot analysis was performed as described by Lagos-Quintana et al., 2002, supra, using 20 µg of total RNA. As a loading control, tRNA was detected by ethidium bromide staining of the gels prior to transfer. MiR-155 was detected using a [$^{32}$P] 5' end-labeled Northern probe having a sequence complementary to the human miR-155 sequence (5'-CCCCT-ATCAC-GATTA-GCATT-AA-3', SEQ ID NO: 5).

As shown in FIG. 3A, cells of the GC-related DLBCL line OCI-Ly1 were found to express only low levels of BIC RNA (which is consistent with results obtained by van den Berg et al., 2003, supra), while cells of non-GC DLBCL lines were found to express intermediate (OCI-Ly8) or very high (OCI-Ly3) levels of BIC RNA. The higher levels of BIC RNA observed in non-GC DLBCL cells may be related to their more active ABC phenotype. Two other EBV-immortalized lymphoblastoid lines (LCLs) that resemble in vitro activated B-cells—JY25 and CB33—were also found to express high levels of BIC RNA. Higher BIC RNA levels appeared to be independent of EBV infection, since higher levels of BIC RNA were observed in the EBV-negative Hodgkin lymphoma (HL) cell lines L428, KMH2 and L1236 as well as the EBV-positive HL cell line L591 (FIG. 3A). While an elevated BIC RNA was detected in human T-cell leukemia virus Type-1 (HTLV-1) transformed T cells (HUT102), elevated levels of BIC RNA were not detected in hematopoietic cell lines such as U266 (myeloma), Jurkat (pre-T), K562 (chronic myelogenous leukemia), or HL60 (acute promyelocytic leukemia), or non-hematopoietic cell lines such as HEK293T (human embryonic kidney). The results obtained in semi-quantitative RT-PCR analysis were consistent with previous observations that BIC RNA accumulates during activation of B and T cells (Haasch et al., 2002, supra; Metzler et al., 2004, supra; van den Berg et al., 2003, supra).

As shown in FIG. 3B, the mature ~22 nucleotide miR-155 was detected only in cells that expressed BIC RNA. In some samples, the predicted ~60 nucleotide pre-miR-155 could also be detected as a weak band. The levels of accumulated miR-155, like those of BIC RNA, were found to differ between cell lines, and changes in the relative levels of miR-155 and BIC RNA resembled each other qualitatively.

Example 2

Processing of BIC Transcripts into miR-155

To test whether BIC transcripts can be processed into miR-155, HEK293T cells were transfected with the plasmid pcDNA3.BIC, which contains a CMV promoter driving synthesis of a 417 nucleotide RNA starting ~90 nucleotides upstream (5') of the miR-155 coding sequence (FIG. 2). The pcDNA3.BIC plasmid was generated by PCR amplification of the BIC exon 3 sequence using 5' and 3' primers that incorporate flanking Nhe I and Xba I sites. The product of this amplification reaction was digested with Nhe I, the Nhe I overhang was filled in using Klenow fragment, the PCR product was digested with Xba I, and the digested PCR product was then subcloned into the pcDNA3 (Invitrogen) vector. Prior to ligation with the BIC insert, pcDNA3 was digested with EcoR I, the EcoR I overhang was filled in using Klenow fragment, and the vector was digested with Xba I. The final pcDNA3.BIC construct was confirmed by sequencing.

As shown in FIG. 3C, cells transfected with this plasmid produced readily detectable amounts of mature miR-155, providing support for the idea that a non-spliced, partial copy of BIC RNA can be processed into miR-155. The results obtained in this experiment were consistent with recent studies of other similarly truncated human miRNA genes (Chen et al., 2004, *Science* 303:83-86).

Example 3

Intracellular Localization of BIC RNA and miR-155

While intron-free BIC RNA can be processed into miR-155, it is unclear whether the normal substrates for the endonuclease Drosha are the primary ~12 kb transcript or the spliced ~1.7 kb BIC RNA detected by Northern blot analysis or RT-PCR amplification (Haasch et al., 2002, supra; Metzler et al., 2004, supra; van den Berg et al., 2003, supra; Tam, 2001, supra; see Example 1). Although it lacks a long open reading frame, BIC RNA resembles mRNA in that it is both spliced and poly-adenylated, suggesting that the spliced transcript may be rapidly exported to the cytoplasm via an mRNA export pathway (Erkmann et al., 2004, *Exp. Cell Res.* 296:12-20).

The intracellular localization of BIC RNA was determined by RT-PCR analysis of total RNA isolated from the cytoplasmic and nuclear fractions of OCI-Ly3 and L1236 cells using primers specific for unspliced or spliced BIC RNA (FIG. 2). Specifically, RNA isolated from OCI-Ly3 and L1236 cells was reverse-transcribed and then PCR amplified using primers specific for spliced BIC RNA (primers A and C; see Example 1), which generates a PCR product of 476 bp, or unspliced BIC RNA (primers C and B, 5'-CTGTC-ACTCC-AGCTT-TATAA-CCGC-3', SEQ ID NO: 6), which generates a PCR product of 467 bp. Control reactions were performed without reverse transcriptase and in the absence of template.

As expected, the unspliced BIC transcript was found to be predominantly nuclear (FIG. 4A), while the much more abundant spliced transcript was found to be primarily cytoplasmic, and hence no longer accessible to the nuclear Drosha microprocessor complex. Thus, most of the detectable BIC RNA cannot be processed into miR-155 by any recognized miRNA processing pathway (Cullen, 2004, supra).

The intracellular localization of miR-155 was determined by Northern blot analysis of total RNA isolated from the cytoplasmic and nuclear fractions of OCI-Ly3 and L1236 cells using a probe having a sequence complementary to the human miR-155 sequence (see Example 1). Pre-miR-155 (predicted to be ~62 nucleotides in length) was detected only in the nuclear fractions (FIG. 4B), indicating that it is processed rapidly after export to the cytoplasm. The detection of mature miR-155 in both the nuclear and cytoplasmic fractions parallels the distributions described in the literature for other miRNAs (Zeng et al., 2003, *RNA* 9:112-23; Meister et al., 2004, *Mol. Cell* 15:185-97). The presence of mature miR-155 in the nuclear fraction may also be due, in part, to contamination of nuclei by perinuclear cytoplasm, which is rich in miRNAs.

Example 4

Invader® mRNA and miR-155 Assays

As described in Example 3, most of the BIC RNA that can be detected in cells is cytoplasmic, and therefore, unlikely to serve as a precursor for miR-155. As a result, BIC RNA levels may not be valid predictors of miR-155 levels. To analyze the relationship between cellular levels of BIC RNA and miR-155, Invader® mRNA and miRNA assays were used to quantify BIC RNA and miRNA in cultured lymphoma cell lines. Unlike other types of miRNA measurements (Calin et al., 2004, *Proc. Natl. Acad. Sci. U.S.A.* 101:11755-60), Invader® miRNA assays require very small amounts of total RNA (20-80 ng) and directly measure the ~22 nucleotide miRNA but not hairpin precursors or primary transcripts. In fact, Invader® assays allow for accurate quantification of mRNA and miRNA molecules in as little as 0.1-20 ng total cellular RNA, depending on the type of RNA being measured and its expression level (Allawi et al., 2004, supra; Eis et al., 2001, supra).

Figure 5:
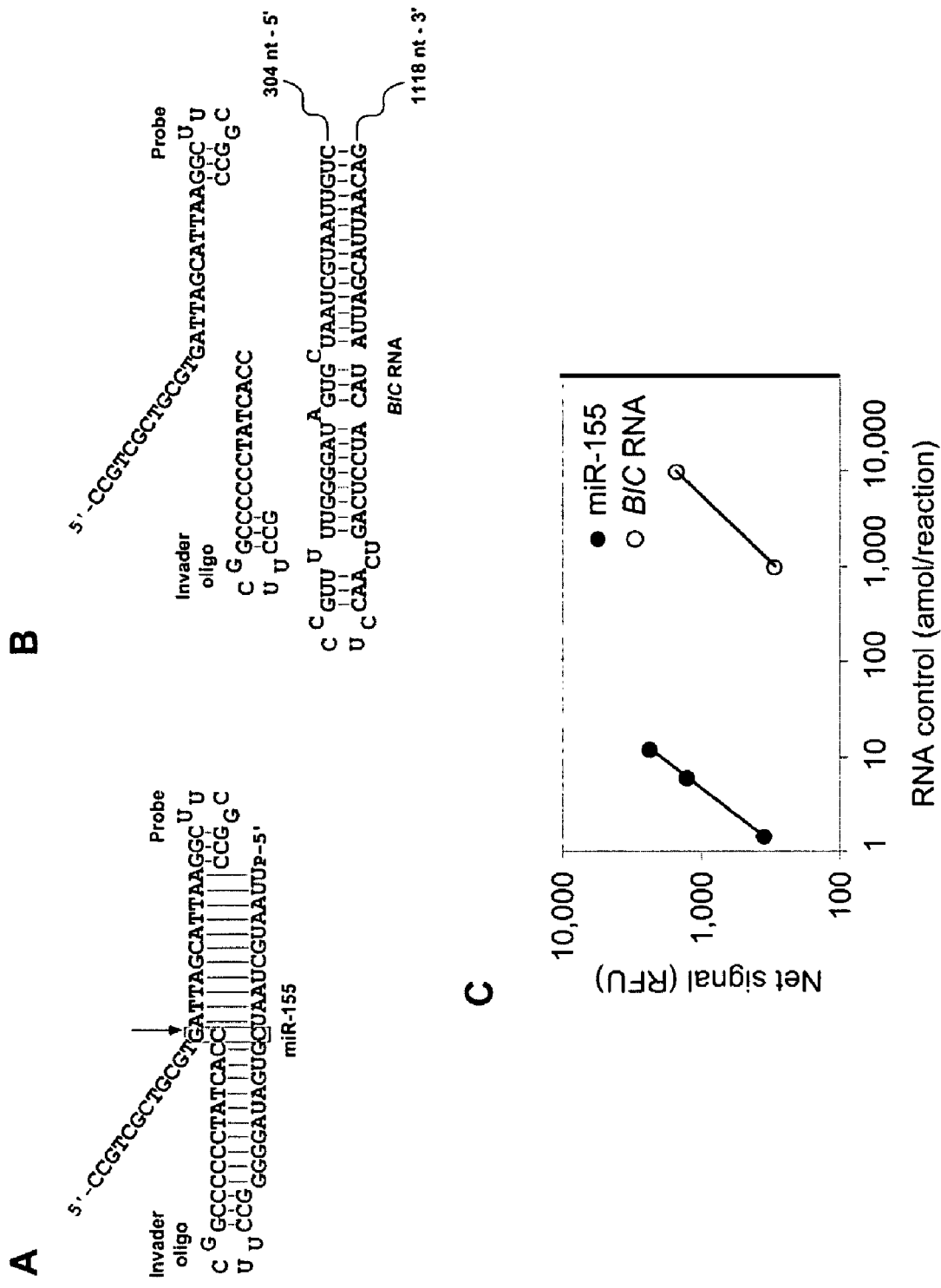
FIGS. 5A-5C show (5A) hybridization between the Invader® oligonucleotide (SEQ ID NO: 42) and probe (SEQ ID NO: 16), which contain 2'-O-methylated hairpins at their 5' and 3' ends, respectively (Allawi et al., 2004, *RNA* 10:1153-61), and miR-155 (SEQ ID NO: 41); the overlap structure (boxed), formed upon binding of the Invader® oligonucleotide and probe to miR-155, enables cleavage (vertical arrow) of the probe's non-complementary 5' arm, which is detected in a subsequent FRET-based Invader® reaction (Eis et al., 2002, *Nat. Biotechnol.* 20:307; Eis et al., 2001, *Nat. Biotechnol.* 19:673-76); (5B) the disruption of this complex by an internal hairpin in BIC RNA (SEQ ID NO: 43), wherein a pre-miR-155 hairpin precludes effective binding of the Invader® oligonucleotide (SEQ ID NO: 42) and probe (SEQ ID NO: 16), greatly reducing cleavage of the probe; and (5C) the specificity of the miR-155 Invader® assay for mature miR-155 over its BIC RNA precursor.

The Invader® probes used for detection of BIC mRNA were specific for the spliced RNA and did not detect unspliced precursor. Other probes that measured the spliced plus unspliced BIC RNA transcripts yielded comparable copy numbers, confirming that the precursor of BIC RNA was present in very low amounts. The miRNA Invader® assay was specific for the mature miR-155 (Allawi et al., 2004, supra) (FIG. 5). Invader® assays for detection of spliced BIC RNA (splice junction 2-3), both spliced and unspliced BIC RNA (exon 3), and mature miR-155 were developed according to published methods (Allawi et al., 2004, supra; Eis, 2002, supra; Eis et al., 2001, supra; Wagner et al., 2003, *RNA* 9:1552-61). Invader® probe set oligonucleotides (Table I) and secondary reaction templates (SRTs) were synthesized by IDT (Coralville, Iowa) and gel purified as described for synthetic miRNAs. FRET oligonucleotides were synthesized and HPLC-purified by the University of Wisconsin Biotechnology Center using phosphoramidites from Glen Research (Sterling, Va.). Oligonucleotide concentrations were calculated from $A_{260nm}$ measurements and the extinction coefficients provided by the oligo manufacturer.

TABLE I

| Assay[1] | Detection[2] | Oligo Type[3] | Sequence & Modifications[4] | SEQ ID NO: |
|---|---|---|---|---|
| BIC RNA (splice junction 2-3) | FAM/Arm 2 | I | cccttcctggtttgtgccaa | 7 |
| | | P | ccgtcacgcctcccattagagcc-(amine) | 8 |
| | | S | AUCUCCAUUGGGUGG | 9 |
| | | A | GGCUCUAAUGGGAGGCG | 10 |
| BIC RNA (exon 3) | | I | agaagtggaaaggtagattctctgcta | 11 |
| | | P | ccgtcacgcctccgcacaacc-(amine) | 12 |
| | | S | GUAUUAUGUGGCUAAGC | 13 |
| | | A | GGUUGUGCGGAGGCG | 14 |
| miR-155 | FAM/Arm 3 | I | GGCUUCGGCCccccctatcacc | 15 |
| | | P | ccgtcgctgcgtgattagcattaaGGCUUCGGCC | 16 |
| | | A | UUAAUGCUAAUCACGCAG | 17 |
| miR-15a | FAM/Arm 1 | I | GGCACUUUUGUGCCcacaaaccattc | 18 |
| | | P | aacgaggcgcacatgtgctgctaCGAGUUUUCGUCG | 19 |
| | | A | UAGCAGCACAUGUGCGC | 20 |
| miR-16 | FAM/Arm 1 | I | GGCACUUUUGUGGGcgccaatattg | 21 |
| | | P | aacgaggcgcactacgtgctgctaCGAGUUUUCGUCG | 22 |
| | | A | UAGCAGCACGUAGUGCGC | 23 |
| let-7a | FAM/Arm 3 | I | GGCACUUUUGUGCCaactatacaact | 24 |
| | | P | ccgtcgctgcgtctactacctcaCGAGUUUUCGUCG | 25 |
| | | A | UGAGGUAGUAGACGCAG | 26 |
| U6 RNA | Red/Arm 4 | I | catccttgcgcaggggccatga | 27 |
| | | P | ccgccgagatcacctaatcttctgctgtat-(amine) | 28 |
| | | A | AUACAGAGAAGAUUAGGUGAUC | 29 |
| Universal | FAM | FRET | (FAM)-cac-(EQ)-tgcttcgtgg | 30 |
| | Red | FRET | (Red)-ctc-(EQ)-ttctcagtgcg | 31 |
| | FAM/Arm 1 | SRT | ccaggaagcatgtggtgcgcctcgUUU | 32 |
| | FAM/Arm 2 | SRT | ccaggaagcatgtggaggcgtgacGGU | 33 |
| | FAM/Arm 3 | SRT | ccaggaagcatgtgacgcagcgacGGU | 34 |
| | FAM/Arm 4 | SRT | cgcagtgagaatgaggtgatctcggcGGU | 35 |

[1] Invader® assays (Third Wave Technologies, Inc.; Madison, WI) were designed using microRNA sequences obtained from the miRNA Registry website. GenBank® Accession No. AF402776 was used for the BIC RNA sequence; GenBank® Accession No. X59262 was used for the U6 RNA sequence. Universal oligonucleotides are used in the secondary reaction of the Invader® assay and can be used interchangeably depending on the 5' arm sequence used on the probe.
[2] Invader® assay detection systems consisted of either FAM or Red FRET oligonucleotides used in combination with an SRT specific for the probe's 5' arm sequence and the FRET oligonucleotide sequence.
[3] Oligonucleotide types included: Invader® oligonucleotide (I), probe (P), stacking oligonucleotide (S), arrestor oligonucleotide (A), FRET oligonucleotide (FRET), and secondary reaction template (SRT).
[4] Natural deoxyribonucleotides are indicated in lower case and 2'-O-methylated nucleotides are indicated in upper case; non-complementary 5' arm portions of probe (P) sequences are indicated in bold; BIC and U6 probes have 3'-amines (amine); FAM is a fluorescein derivative, Red is Redmond Red™ dye, and EQ is Eclipse Quencher™ dye (Epoch BioSciences; Bothell, WA).

Invader® miRNA Assay Generic Reagents kits (Third Wave Technologies, Inc.; Madison, Wis.) were used as recommended to prepare primary reactions (10 µL) containing 20-40 ng of total RNA from a selected cell and either 5 pmol Invader® oligonucleotide, 8 pmol probe, and 3 pmol Stacking oligonucleotide for BIC RNA assays; 5 pmol each of Invader® oligonucleotide and probe for miR-155 assays; or 10 pmole each of Invader® oligonucleotide and probe for miR-15a, miR-16, and let-7a assays. Secondary reactions (15 µL) contained a 4-fold molar excess of the appropriate Arrestor oligonucleotides, 10 pmol FRET oligonucleotide, and 2.5 pmol SRT. Invader® reactions were set up in 96-well 0.2 µL microplates (BioExpress; Kaysville, Utah), and primary reactions were incubated for 90 minutes at either 60° C. for BIC RNA, 44° C. for miR-155, 54° C. for miR-15a and miR-16, or 49° C. for let-7a. Secondary reactions were initiated by adding the FRET oligonucleotide, SRT, and appropriate arrestor oligonucleotide, and then incubating the reaction mixture at 60° C. for a total of 60 minutes, with measurements of the fluorescence signal taken at 15, 30, and 60 minutes. A GENios plate reader (Tecan U.S.; Durham, N.C.) was used to measure FAM fluorescence (excitation 485/20 nm and emission 530/25 nm bandpass filters) or Red fluorescence (excitation 560/20 nm and emission 620/40 nm bandpass filters) with a 40 µs integration time. All reactions were performed in triplicate except where noted. Replicate measurements were averaged and corrected for background signal (measured using 100 ng tRNA per reaction) before calculating RNA amounts from miRNA and BIC RNA standard curves (using a range of 1.5-24 amol synthetic miR-155 per reaction and 0.15-2.4 amol for BIC) as described previously (Eis et al., 2001, supra; Wagner et al., 2003, supra).

Figure 6:
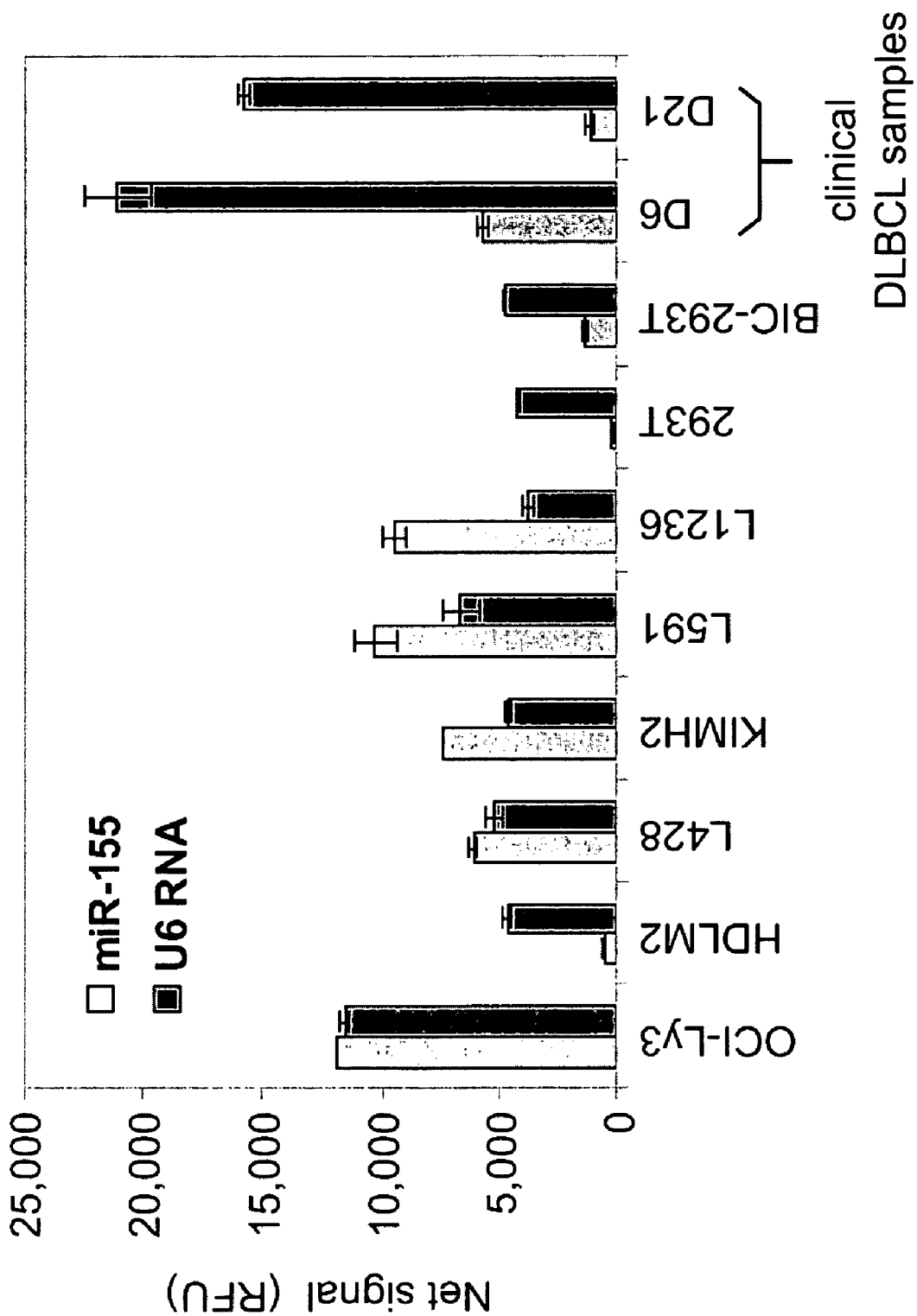
FIG. 6 shows the levels of miR-155 and U6 RNA in six cultured lymphoma cell lines, HEK293T cells, HEK293T cells transfected with pcDNA3.BIC, and two clinical DLBCL samples as determined in biplex format Invader® assays (Eis et al., 2002, supra; Eis et al., 2001, supra) using a fixed amount (40 ng) of total cellular RNA from each sample; data was plotted using net signal values (background subtracted using the tRNA signal); error bars represent one standard deviation.

Because significant variations in the expression of U6 RNA (>5 fold) were observed in a number of cell types (FIG. 6), U6 RNA was not used as an internal standard for normalization of miRNA expression. These variations are likely due to differences in the activity of RNA polymerase III in transformed cells (Hirsch et al., 2004, *Mol. Cell. Biol.* 24:5989-99; White, 2004, *Oncogene* 23:3208-16). Thus, in calculating the RNA copy number per cell, a total of 20 pg RNA per cell was assumed (Alberts et al., *Molecular Biology of the Cell* (Garland Publishing, Inc., 1994)). Expression of BIC RNA and miR-155 in control U266 cells was undetectable in Invader® assays (i.e., less than ~10 copies/cell of BIC RNA and ~50 copies/cell of miR-155).

Suitable standards for miRNA Invader® assays were designed using sequences disclosed in the miRNA Registry (Griffiths-Jones, 2004, *Nucleic Acid Res.* 32:D109-11). MiRNA standards were synthesized by Dharmacon (Lafayette, Colo.). Deprotected synthetic miRNAs were gel purified on 20% denaturing (7M urea) polyacrylamide gels; eluted with 10 mM Tris, pH 8, 0.1 mM EDTA buffer; and desalted in DEPC-treated water (GeneMate; ISC BioExpress; Kaysville, Utah) on NAP-10 columns (Amersham Biosciences; Piscataway, N.J.). Concentrations of synthetic miRNA standards were determined using the following $e_{260nm}$ values provided by Dharmacon: miR-155, 229,800; miR-15a, 225,700; miR-16, 226,100; and let-7a, 237,700.

Suitable standards for BIC RNA Invader® assays were prepared by T7 in vitro transcription using a template generated by RT-PCR amplification of total RNA obtained from Raji cells using a MasterAmp High Fidelity RT-PCR kit (EpiCentre, Madison, Wis.). Amplification reactions were performed by adding 5 µg of DNase-treated total RNA and the primers 5'-TAATA-CGACT-CACTA-TAGGG-AGCGG-AGCCC-CGAGC-CG-3' (SEQ ID NO: 36), which contains T7 promoter sequence, and 5'-CTCAT-GAGAT-TTATT-TG-GTT-ACAGT-GAATA-ACCTG-G-3' (SEQ ID NO: 37) to a reaction volume of 50 µL. A near full-length BIC transcript (1410 nucleotides) was prepared from the resulting PCR product using a T7 Ampliscribe transcription kit (Epicentre, Madison, Wis.). Following synthesis, the BIC transcript was gel purified on a 5% denaturing (8M urea) acrylamide gel; eluted with 10 mM Tris, pH 7.6, 0.3 M NaCl, 10 mM EDTA, 0.5% SDS buffer; and desalted and concentrated by phenol: chloroform extraction and ethanol precipitation. Absorbance measurements at 260 nm were used to calculate the concentration of BIC RNA, assuming 1 $A_{260nm}$ unit=40 ng/µL and a MW of 452,064 Da.

Example 5

Quantification of BIC RNA and miR-155 in Cultured Lymphoma Cell Lines

As described in Example 3, most of the BIC RNA that can be detected in cells is cytoplasmic, and therefore, unlikely to serve as a precursor for miR-155. As a result, BIC RNA levels may not be valid predictors of miR-155 levels. To analyze the relationship between cellular levels of BIC RNA and miR-155, Invader® assays were used to quantify BIC RNA and miRNA in cultured lymphoma cell lines.

Figure 7:
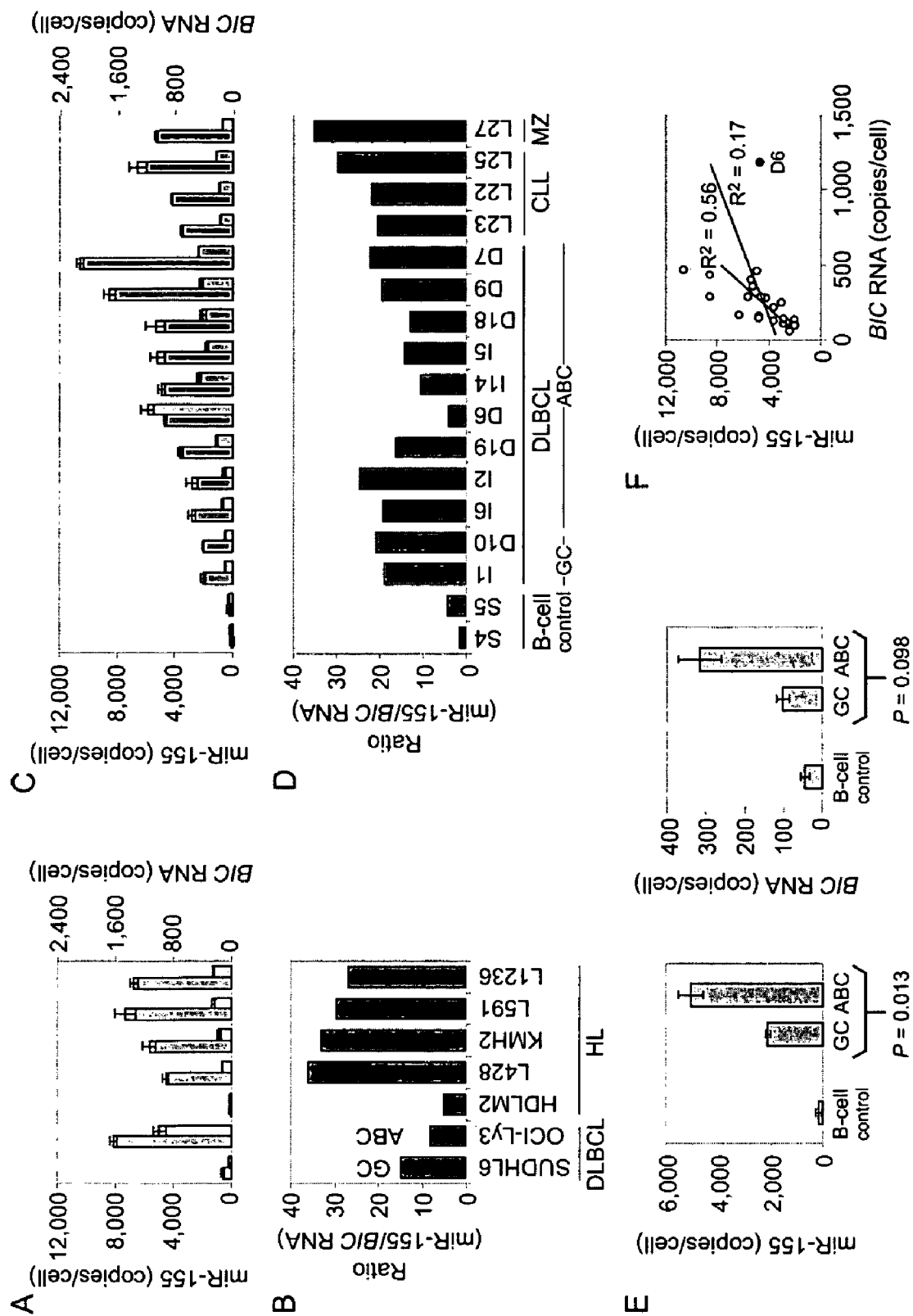
FIGS. 7A-7F show (7A) the levels of miR-155 and BIC RNA in several cultured lymphoma cell lines as determined in Invader® mRNA and miR-155 assays, wherein the first bar in each pair represents the number of miR-155 copies per cell and the second bar in each pair represents the number of BIC RNA copies per cell, and wherein error bars represent one standard deviation; (7B) the ratios of miR-155 copy number to BIC RNA copy number in the cultured lymphoma cell lines shown in FIG. 7A; (7C) the levels of miR-155 and BIC RNA in clinical B-cell lymphoma isolates, wherein the first bar in each pair represents the number of miR-155 copies per cell and the second bar in each pair represents the number of BIC RNA copies per cell, and wherein error bars represent one standard deviation; (7D) the ratios of miR-155 copy number to BIC RNA copy number in the clinical B-cell lymphoma isolates shown in FIG. 7C; (7E) a comparison of the miR-155 (first panel) and BIC RNA (second panel) copy numbers in DLBCL cells exhibiting either the GC or ABC phenotype, wherein p values were calculated from a t-test between the GC phenotype (n=4) and the ABC phenotype (n=19) using the statistical package Statview (SAS Institute, Inc.), and wherein error bars represent one standard error; (7F) the lack of correlation between the amounts of miR-155 and BIC RNA in clinical B-cell lymphoma isolates, wherein linear regression analysis was performed with and without sample D6 (filled circle) (DLBCL=diffuse large B-cell lymphoma, HL=Hodgkin lymphoma, GC=germinal center-cell like, ABC=activated B-cell-like; CLL=chronic lymphocytic leukemia; MZ=marginal zone B-cell lymphoma).

Invader® mRNA and miR-155 assays yielded copy numbers in selected cell lines of between ~20 and ~1,000 BIC RNA molecules and between ~100 and ~8,000 miR-155 molecules (FIG. 7A; Table II). The levels of BIC RNA and miR-155, as quantified by the Invader® assays, were consistent with the results of semi-quantitative RT-PCR and Northern blot analysis. Notably, the molar ratios of miR-155 to BIC RNA, which varied from ~5 to ~30 (FIG. 7B), did not correlate with the absolute copy numbers of BIC RNA and miR-155, which may be due to differences in the synthesis, processing, nuclear export, and turnover rates of BIC RNA and miR-155.

TABLE II

| Sample | | | BIC RNA | | miR-155 | |
|---|---|---|---|---|---|---|
| Name | Type | IHC[1] | copies/cell | $SD^2$ | Copies/cell | $SD^2$ |
| SUDHL6 | DLBCL cell line | GC-like | 38 | 11 | 570 | 120 |
| OCI-Ly3 | DLBCL cell line | ABC-like | 990 | 84 | 8,100 | 230 |
| HDLM2 | Hodgkin cell line | | 22 | 5 | 110 | 20 |
| L428 | Hodgkin cell line | | 130 | 1 | 4,500 | 220 |
| KMH2 | Hodgkin cell line | | 170 | 27 | 5,700 | 450 |
| L591 | Hodgkin cell line | | 250 | 18 | 7,400 | 730 |
| L1236 | Hodgkin cell line | | 250 | 7 | 6,700 | 280 |

[1]IHC = immunohistochemistry.
[2]SD = standard deviation.

Previous in situ hybridization studies have shown that the amount of BIC RNA in DLBCL cells is very low or undetectable (van den Berg et al., 2003, supra). However, the Invader® assays showed that detectable amounts of both BIC RNA and miR-155 were present in SUDHL6 cells, a prototypic GC-type DLBCL line, and that the levels of BIC RNA and miR-155 were ~25 and ~15 fold higher, respectively, in OCI-Ly3 cells, a prototypic ABC-type DLBCL line (FIG. 7A). Thus, BIC RNA and miR-155 are detectable in both DLBCL types, but are particularly elevated in cells with the ABC phenotype. Moreover, in contrast with results obtained by van den Berg et al., 2003, supra, which indicated that elevated BIC RNA expression was limited to Hodgkin lymphomas, elevated levels of both BIC RNA and miR-155 were detected in several types of B-cell lymphomas.

Example 6

Quantification of BIC RNA and miR-155 in Clinical B-Cell Lymphomas

To determine if the levels of BIC RNA and miR-155 were also elevated in clinically isolated DLBCL cells, Invader® assays were used to quantify BIC RNA and miR-155 in 23 clinically isolated DLBCL samples. Normal, circulating CD19+ B-cells (samples S4 and S5 in Table III below), in which BIC RNA expression has been shown to increase upon mitogen stimulation, were used as controls.

DLBCL, chronic lymphocytic leukemia (CLL), and marginal zone B-cell lymphoma (MZ) tissue samples were obtained from the Department of Pathology at the Weill Medical College of Cornell University. Specimens were obtained from patients according to the protocol approved by the Investigational Review Board (IRB), and all lymphoma cases were reviewed and classified according to the World Health Organization (WHO) classification. For DLBCL samples, only de novo cases were selected. Human B-cell controls were purified from the lymphocyte fraction of whole blood (buffy coat) obtained from human donors by positive selection using CD19+ beads (MACS; Miltenyi Biotec), and cultured in RPMI medium with 10% fetal calf serum.

Immunohistochemical analyses were performed on representative sections of formalin-fixed paraffin-embedded tissues from DLBCL cases by staining with antibodies against phenotypic markers BCL-6, CD10, MUM1/IRF4, and CD138, using the avidin-biotin-peroxidase technique with antigen epitope enhancement by pressure cooker heating (Chang et al., 2004, supra). Each marker was considered positive if >20% of the neoplastic lymphocytes were stained positive. DLBCL cases were classified as GC cases if they were positive for BCL-6 and/or CD10, but negative for MUM-1 and CD138, and as ABC cases if they were positive for MUM-1 and +/− for BCL-6, CD10, and CD138.

Relative to the control B-cells, BIC RNA levels were elevated 2 to 10 fold in DLBCL cells, with one sample (D6) showing an increase of >20 fold (FIG. 7C). MiR-155 levels were increased to even greater extents, generally ~12 to ~30 fold, but ranging as high as 50 to 60 fold for samples I9, D7, and D9 (~8,500 to 10,000 copies per cell) (Table III). Significantly, the levels of both miR-155 and BIC RNA were, on average, 2 to 3 fold higher in DLBCL cells with the ABC phenotype than in DLBCL cells with the GC phenotype (FIG. 7E). Thus, the levels of miR-155 (and BIC RNA) appear to correspond with clinically significant DLBCL subtypes, suggesting that quantification of miR-155 levels may be a useful prognostic indicator.

TABLE III

| Sample | | | BIC RNA | | miR-155 | |
|---|---|---|---|---|---|---|
| Name | Type | IHC[1] | copies/cell | SD[2] | Copies/cell | SD[2] |
| S4[3] | B-cell | | 33 | 15 | 51 | 130 |
| S5 | B-cell | | 56 | 6 | 250 | 180 |
| I1 | DLBCL | GC | 110 | 10 | 2,000 | 150 |
| D10 | DLBCL | GC | 99 | 8 | 2,100 | 36 |
| I3 | DLBCL | GC | 140 | 10 | 2,100 | 50 |
| D16 | DLBCL | GC | 64 | 6 | 2,400 | 120 |
| I6 | DLBCL | ABC | 150 | 21 | 2,800 | 260 |
| I2 | DLBCL | ABC | 120 | 26 | 2,800 | 410 |
| D19 | DLBCL | ABC | 220 | 20 | 3,600 | 140 |
| D6 | DLBCL | ABC | 1,180 | 84 | 4,700 | 80 |
| I14 | DLBCL | ABC | 470 | 31 | 4,900 | 260 |
| I5 | DLBCL | ABC | 360 | 30 | 5,200 | 550 |
| D18 | DLBCL | ABC | 410 | 35 | 5,400 | 710 |
| D9 | DLBCL | ABC | 440 | 28 | 8,500 | 370 |
| D7 | DLBCL | ABC | 480 | 14 | 10,500 | 260 |
| I12 | DLBCL | ABC | 120 | 1 | 2,600 | 100 |
| D17 | DLBCL | ABC | 250 | 5 | 3,000 | 110 |
| D2 | DLBCL | ABC | 130 | 10 | 3,600 | 400 |
| I4 | DLBCL | ABC | 290 | 4 | 4,200 | 100 |
| D13 | DLBCL | ABC | 300 | 30 | 4,600 | 290 |
| D5 | DLBCL | ABC | 170 | 20 | 4,700 | 100 |
| D12 | DLBCL | ABC | 150 | 20 | 4,800 | 10 |
| I10 | DLBCL | ABC | 300 | 10 | 5,600 | 70 |
| I8 | DLBCL | ABC | 180 | 10 | 6,200 | 80 |
| I9 | DLBCL | ABC | 290 | 20 | 8,500 | 70 |
| L23 | CLL | | 170 | 13 | 3,500 | 110 |
| L22 | CLL | | 190 | 8 | 4,200 | 45 |
| L25 | CLL | | 220 | 3 | 6,600 | 610 |
| L27 | MZ | | 150 | 1 | 5,300 | 100 |

[1]Immunohistochemistry (IHC) - DLBCL cases were classified as follows: GC cases were positive for BCL-6 and/or CD10, but negative for MUM-1 and CD138, and ABC cases were positive for MUM-1 and +/− for BCL-6, CD10, and CD138.
[2]SD = standard deviation.
[3]miR-155 was not significantly detected over background in sample S4.

For comparison, three CLL cases and one MZ case were also analyzed (FIG. 7C). In all cases, miR-155 and BIC RNA levels were comparable to those observed for DLBCL cells with the ABC phenotype, indicating that increased accumulation of miR-155 and BIC RNA is likely to be a common feature of B-cell lymphomas. The observation of increased miR-155 levels (~2,000-10,000 copies per cell vs. ~150 in normal circulating B-cells) in both aggressive (DLBCL) and more indolent (CLL and MZ) lymphomas, as well as in both non-Hodgkin and Hodgkin lymphomas, suggests that miR-155 may play a more general role in the pathogenesis of B-cell lymphomas in general.

It has been suggested that the amount of BIC RNA in clinical samples can serve as an indirect measure of miR-155 (Metzler et al., 2004, supra). To examine the predictive value of BIC RNA levels, the molar ratios of BIC RNA and miR-155 in clinical samples were determined (FIG. 7D). These molar ratios were found to range greatly, from ~4 to ~25 fold. A regression plot (FIG. 7F) showed only a weak correlation ($R^2=0.17$) between the levels of miR-155 and BIC RNA, even when sample D6 was excluded ($R^2=0.56$). These data indicate that the amount of BIC RNA in a cell should not be taken as an accurate measure of the amount of miR-155 in the cell, particularly since miR-155 is likely to be the active gene product of the BIC RNA transcript.

Because miRNAs act as post-transcriptional down-regulators of gene expression, an elevated level of miR-155 might directly or indirectly reduce the synthesis of a protein with tumor suppressor or pro-apoptotic function. Recently, the mRNA of transcription factor PU.1, which is required for late differentiation of B-cells (Loddenkemper et al., 2004, *J. Pathol.* 202:60-69), was identified as a possible target for miR-155 (John et al., 2004, supra). Similar miR-155 target sequences can be identified in the 3' UTRs of PU.1 mRNA molecules from other mammals and chickens (FIG. 8). In addition, the mRNA of another transcription factor that is controlled during B-cell development, C/EBP/β (Xie et al., 2004, *Cell* 117:663-76), has a potential target site for miR-155 in its 3' UTR (FIG. 8).

Example 7

Quantification of Other MiRNA Molecules

Figure 9:
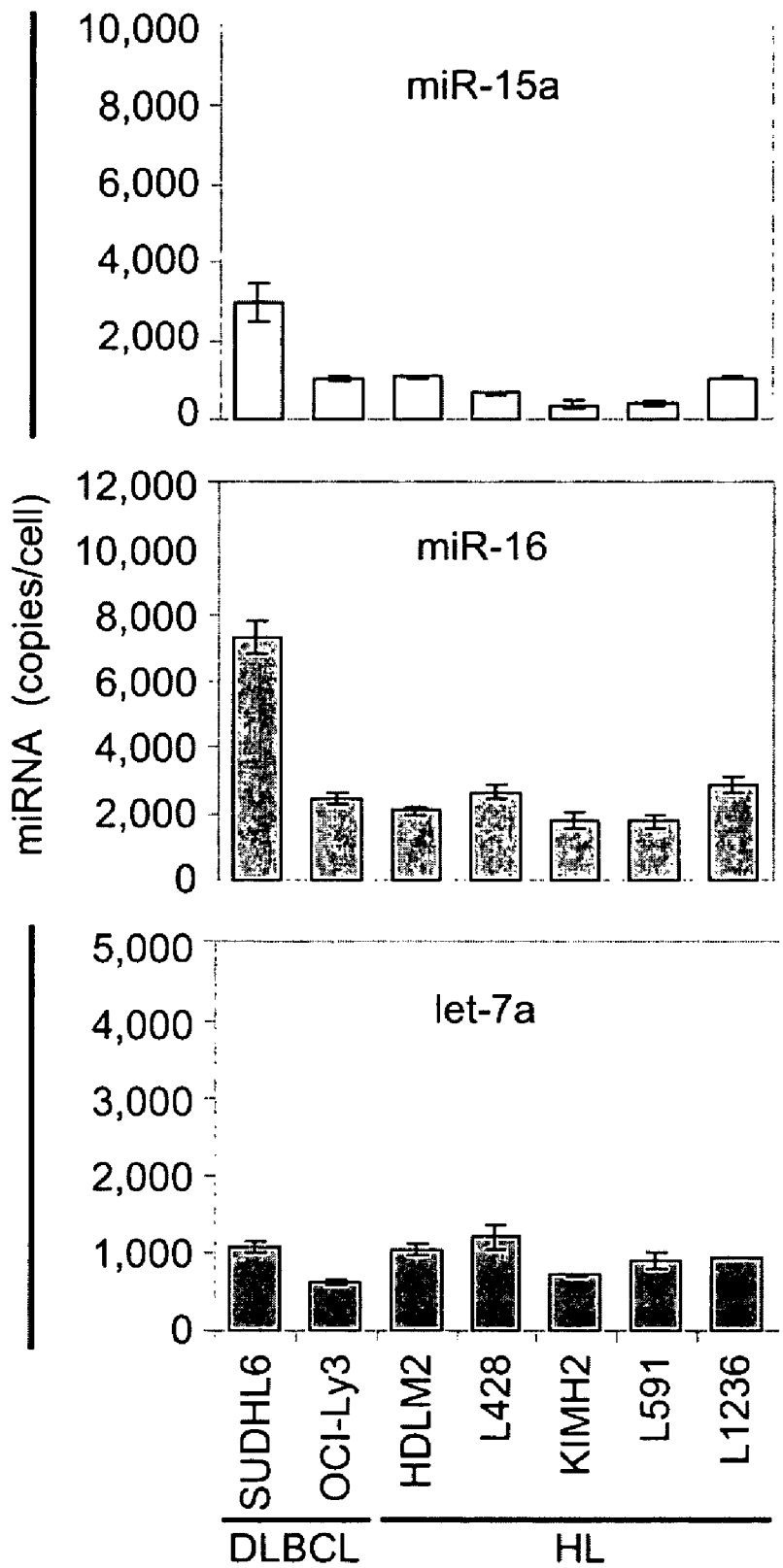
FIG. 9 shows the levels of miR-15a, miR-16, and let-7a in cultured lymphoma cell lines as determined in Invader® miRNA assays (DLBCL=diffuse large B-cell lymphoma, HL=Hodgkin lymphoma).

Recently, the levels of miR-15a and miR-16 have been reported to be reduced in clinical isolates of CLL cells (Calin et al., 2002, supra), and lower levels of let-7a RNA have been detected in lung cancer biopsies having a poor clinical outcome (Takamizawa et al., 2004, supra). To determine whether lymphoma cells exhibited similar changes, Invader® miR-155 assays were used to quantify miR-15, miR-16, and let-7a levels in cultured lymphoma cell lines and clinical B-cell lymphoma isolates (FIGS. 9 and 10; Table IV).

TABLE IV

| Sample | | | miR-15a | | miR-16 | | let-7a | |
|---|---|---|---|---|---|---|---|---|
| Name | Type | IHC[1] | copies/cell | SD[2] | Copies/cell | SD[2] | Copies/cell | SD[2] |
| SUDHL6 | DLBCL cell line | GC-like | 3,000 | 490 | 7,300 | 450 | 1,100 | 68 |
| OCI-Ly3 | DLBCL cell line | ABC-like | 1,100 | 52 | 2,500 | 170 | 630 | 36 |
| HDLM2 | Hodgkin cell line | | 1,100 | 55 | 2,100 | 110 | 1,100 | 77 |

TABLE IV-continued

| Sample | | | miR-15a | | miR-16 | | let-7a | |
|---|---|---|---|---|---|---|---|---|
| Name | Type | IHC[1] | copies/cell | SD[2] | Copies/cell | SD[2] | Copies/cell | SD[2] |
| L428 | Hodgkin cell line | | 670 | 47 | 2,600 | 220 | 1,200 | 150 |
| KMH2 | Hodgkin cell line | | 380 | 86 | 1,800 | 220 | 720 | 5 |
| L591 | Hodgkin cell line | | 410 | 55 | 1,800 | 190 | 910 | 97 |
| L1236 | Hodgkin cell line | | 1,100 | 11 | 2,900 | 230 | 950 | 3 |
| S4 | B-cell | | 7,700 | 350 | 8,600 | 190 | 2,300 | 43 |
| S5 | B-cell | | 7,100 | 450 | 8,900 | 620 | 2,400 | 78 |
| I1 | DLBCL | GC | 1,900 | 110 | 4,000 | 230 | 2,000 | 130 |
| D10 | DLBCL | GC | 8,500 | 140 | 11,300 | 190 | 3,300 | 170 |
| I6 | DLBCL | ABC | 3,300 | 190 | 5,400 | 500 | 3,500 | 140 |
| I2 | DLBCL | ABC | 2,800 | 14 | 5,900 | 550 | 1,200 | 33 |
| D19 | DLBCL | ABC | 2,200 | 57 | 4,500 | 180 | 2,000 | 170 |
| D6 | DLBCL | ABC | 3,700 | 120 | 6,200 | 690 | 2,000 | 62 |
| I14 | DLBCL | ABC | 4,900 | 260 | 8,000 | 330 | 4,500 | 240 |
| I5 | DLBCL | ABC | 4,500 | 350 | 5,900 | 550 | 1,800 | 160 |
| D18 | DLBCL | ABC | 3,000 | 110 | 5,000 | 480 | 2,600 | 14 |
| D9 | DLBCL | ABC | 2,900 | 32 | 5,900 | 220 | 4,000 | 420 |
| D7 | DLBCL | ABC | 4,500 | 260 | 8,900 | 410 | 3,000 | 230 |
| L23 | CLL | | 5,300 | 240 | 7,600 | 740 | 3,800 | 220 |
| L22 | CLL | | 3,700 | 170 | 7,400 | 780 | 2,700 | 190 |
| L25 | CLL | | 4,900 | 420 | 9,400 | 540 | 4,200 | 420 |
| L27 | MZ | | 1,900 | 73 | 7,400 | 1,200 | 2,000 | 72 |

[1] Immunohistochemistry (IHC) - DLBCL cases were classified as follows: GC cases were positive for BCL-6 and/or CD10, but negative for MUM-1 and CD138, and ABC cases were positive for MUM-1 and +/− for BCL-6, CD10, and CD138.
[2] SD = standard deviation.

Invader® assays were performed as described in Example 4. In most of the DLBCL isolates, miR-15a levels were reduced by about 30-70% as compared to the miR-15a levels in circulating B-cells, miR-16 levels were reduced ~25% on average, and no consistent pattern of change was observed for let-7a. However, in none of the assayed cell lines did the level of any of these miRNA molecules exhibit the ~30 fold increase that was observed for miR-155 (see Examples 5 and 6). In all of the cultured lymphoma cells, particularly the Hodgkin cell lines, lower levels of miR-15a, miR-16, and let-7a were observed than in normal circulating B-cells (Table IV).

It should be understood that the foregoing disclosure emphasizes certain specific embodiments of the invention and that all modifications or alternatives equivalent thereto are within the spirit and scope of the invention as set forth in the appended claims.

What is claimed is:

1. A method for diagnosing B-cell lymphoma in an animal, comprising the steps of:
   (a) determining the amount of miR-155 in a B-cell sample isolated from the animal;
   (b) determining the amount of miR-155 in normal B-cells;
   (c) comparing the amount of miR-155 in the B-cell sample isolated from the animal with the amount of miR-155 in normal B-cells; and
   (d) diagnosing B-cell lymphoma in the animal if the amount of miR-155 in the B-cell sample isolated from the animal is higher than the amount of miR-155 in the normal B-cells, wherein the B-cell lymphoma is diffuse large B-cell lymphoma (DLBCL) or marginal zone (MZ) B-cell lymphoma.

2. The method of claim 1, wherein the B-cell lymphoma is marginal zone (MZ) B-cell lymphoma.

3. The method of claim 1, wherein the B-cell lymphoma is diffuse large B-cell lymphoma (DLBCL).

4. The method of claim 1, wherein the animal is a mammal.

5. The method of claim 1, wherein the mammal is a human.

6. The method of claim 1, wherein an invasive cleavage assay is used to determine the amount of miR-155.

7. The method of claim 1, wherein the normal B-cells are obtained from a healthy individual.

8. The method of claim 1, wherein the normal B-cells are obtained from a cultured cell line.

9. The method of claim 1, wherein the amount of miR-155 in normal B-cells is determined by referring to a reference standard for the amount of miR-155 expression for normal B-cells.

10. The method of claim 1, wherein the amount of miR-155 in the B-cell sample isolated from the animal is at least two times higher than the amount of miR-155 in the normal B-cells.

11. The method of claim 1, wherein the amount of miR-155 in the B-cell sample isolated from the animal is at least ten times higher than the amount of miR-155 in the normal B-cells.

12. The method of claim 3, wherein the diffuse large B-cell lymphoma (DLBCL) is DLBCL with an activated B-cell (ABC) phenotype in an animal.

\* \* \* \* \*

UNITED STATES PATENT AND TRADEMARK OFFICE
CERTIFICATE OF CORRECTION

PATENT NO.       : 7,700,288 B2  
APPLICATION NO.  : 11/352837  
DATED            : April 20, 2010  
INVENTOR(S)      : James E. Dahlberg et al.

Page 1 of 1

It is certified that error appears in the above-identified patent and that said Letters Patent is hereby corrected as shown below:

At item (73) of the cover sheet:

please delete the word "Assignee" and replace it with the word

-- Assignees --, and after "Wisconsin Alumni Research Foundation, Madison, WI (US)," please add -- Cornell Research Foundation, Inc., Ithaca, NY (US) --.

Signed and Sealed this
Twentieth Day of September, 2011

David J. Kappos
*Director of the United States Patent and Trademark Office*